US011597765B2

(12) United States Patent
Mao et al.

(10) Patent No.: US 11,597,765 B2
(45) Date of Patent: Mar. 7, 2023

(54) USE OF SEMAPHORIN-4D BINDING MOLECULES FOR THE TREATMENT OF RETT SYNDROME

(71) Applicants: VACCINEX, INC., Rochester, NY (US); The Sydney Children's Hospital Network, Westmead (AU)

(72) Inventors: Yilin Mao, Westmead (AU); Wendy Gold, Westmead (AU); Elizabeth E. Evans, Bloomfield, NY (US); Maurice Zauderer, Pittsford, NY (US)

(73) Assignees: VACCINEX, INC., Rochester, NY (US); The Sydney Children's Hospital Network, Westmead (AU)

( * ) Notice: Subject to any disclaimer, the term of this patent is extended or adjusted under 35 U.S.C. 154(b) by 10 days.

(21) Appl. No.: 17/352,574

(22) Filed: Jun. 21, 2021

(65) Prior Publication Data
US 2021/0403559 A1 Dec. 30, 2021

Related U.S. Application Data

(60) Provisional application No. 63/043,945, filed on Jun. 25, 2020.

(51) Int. Cl.
*A61K 39/00* (2006.01)
*A61K 39/395* (2006.01)
*C07K 16/28* (2006.01)
*A61P 25/00* (2006.01)

(52) U.S. Cl.
CPC .......... *C07K 16/2803* (2013.01); *A61P 25/00* (2018.01); *A61K 2039/505* (2013.01); *C07K 2317/565* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 4,683,195 A | 7/1987 | Mullis et al. | |
| 4,873,192 A | 10/1989 | Kunkel | |
| 5,225,539 A | 7/1993 | Winter | |
| 5,585,089 A | 12/1996 | Queen et al. | |
| 5,693,761 A | 12/1997 | Queen et al. | |
| 5,693,762 A | 12/1997 | Queen et al. | |
| 5,859,205 A | 1/1999 | Adair et al. | |
| 5,892,019 A | 4/1999 | Schlom et al. | |
| 5,939,598 A | 8/1999 | Kucherlapati et al. | |
| 6,180,370 B1 | 1/2001 | Queen et al. | |
| 6,737,056 B1 | 5/2004 | Presta | |
| 8,496,938 B2 | 7/2013 | Smith et al. | |
| 9,512,224 B2 | 12/2016 | Zauderer | |
| 9,598,495 B2 | 3/2017 | Smith et al. | |
| 10,385,136 B2 | 8/2019 | Smith et al. | |
| 2004/0132101 A1 | 7/2004 | Lazar et al. | |
| 2006/0233793 A1 | 10/2006 | Belin et al. | |
| 2008/0219971 A1* | 9/2008 | Smith | A61P 35/00 435/69.6 |
| 2010/0285036 A1 | 11/2010 | Smith et al. | |
| 2013/0095118 A1 | 4/2013 | Smith et al. | |
| 2015/0110800 A1 | 4/2015 | Smith et al. | |

FOREIGN PATENT DOCUMENTS

| | | | |
|---|---|---|---|
| EP | 0075444 A2 | 3/1983 | |
| EP | 3013350 A1 | 1/2020 | |
| WO | 9314125 A1 | 7/1993 | |
| WO | 0127160 A1 | 4/2001 | |
| WO | 2008100995 A1 | 8/2008 | |
| WO | 2010129917 A2 | 11/2010 | |
| WO | 2018156509 A1 | 8/2018 | |
| WO | 2018204895 A1 | 11/2018 | |
| WO | WO-2018204895 A1 * | 11/2018 | .............. A61P 25/00 |
| WO | 2020198572 A1 | 10/2020 | |

OTHER PUBLICATIONS

Frias et al. Molecular pathway underlying bouton stabilization by Semaphorin4D during inhibitory synapse formation. bioRxiv 100271; doi: https://doi.org/10.1101/100271. (Year: 2017).*
Elhabazi et al. The Human Semaphorin-like Leukocyte Cell Surface Molecule CD100 Associates with a Serine Kinase Activity. JBC vol. 272, No. 38, Issue of Sep. 19, pp. 23515-23520, 1997. (Year: 1997).*
Fisher et al. Generation and preclinical characterization of an antibody specific for SEMA4D. mAbs 8:1, 150-162; Jan. 2016. (Year: 2016).*
Dieffenbach et al., "Per Primer: A Laboratory Manual", Cold Spring Harbor Press, 2003. Abstract.
McGann et al., "Astrocytes conspire with neurons during progression of neurological disease", Curr Opin Neurobiol. 22 (5): 850-858, Oct. 2012.
Maezawa et al., "Rett Syndrome Astrocytes Are Abnormal and Spread MeCP2 Deficiency through Gap Junctions", The Journal of Neuroscience, 29(16): 5051-5061, Apr. 22, 2009.
Skene et al., "Neuronal MeCP2 is expressed at near histone-octamer levels and globally alters the chromatin state", Mol Cell (2010) 37:457-468.
Guy et al., "Reversal of neurological defects in a mouse model of Rett syndrome", Science, 315:1143-1147, 2007.
Ballas et al., "Non-cell autonomous influence of MeCP2-deficient glia on neuronal dendritic morphology", Nat. Neurosci. 12:311-317, 2009.
Gemelli et al., "Postnatal loss of methyl-CpG binding protein 2 in the forebrain is sufficient to mediate behavioral aspects of Rett syndrome in mice", Biol. Psych. 59:468-476, 2006. Abstract.

(Continued)

*Primary Examiner* — Maher M Haddad
(74) *Attorney, Agent, or Firm* — KDB Firm PLLC

(57) ABSTRACT

Provided herein are methods for alleviating symptoms in a subject having Rett syndrome, comprising administering to the subject an effective amount of an isolated binding molecule which specifically binds to semaphorin-4D (SEMA4D).

16 Claims, 17 Drawing Sheets

Specification includes a Sequence Listing.

(56) References Cited

OTHER PUBLICATIONS

Klein, "Immunology: The Science of Self-Nonself Discrimination", John Wiley & Sons, New York, 1982. Abstract.
Lewin, "Genes VIII", Prentice Hall 2003. Abstract.
Kontermann et al., "Antibody Engineering", Springer Verlag, 2001. Abstract.
Abbas et al., "Cellular and Molecular Immunology", 5th ed.; Elsevier Health Sciences Division, 2005. Abstract.
Roitt et al., "Immunology", 6th ed.,London, Mosby, 2001. Abstract.
Goldsby et al., "Kuby Immunology", 4th ed., H. Freeman & Co., 2000. Abstract.
Campbell, "Monoclonal Antibody Technology: The Production and Characterization of Rodent and Human Hybridomas" in Laboratory Techniques in Biochemistry and Molecular Biology, ed. Burden et al., (Elsevier, Amsterdam); 1984. Abstract.
Kennett et al., "Monoclonal Antibodies, Hybridoma: A New Dimension in Biological Analyses", Plenum Press, NY, eds. 1980. Abstract.
Osol et al., "Remington's Pharmaceutical Sciences", Mack Publishing Co., 16th ed. 1980. Abstract.
Clover, "DNA Cloning", vols. I and II, ed. 1985. Abstract.
Cait, ed. 1984, "Oligonucleotide Synthesis: A Practical Approach". Abstract.
Hames and Higgins, "Nucleic Acid Hybridization", eds. 1984. Abstract.
Hames and Higgins, "Transcription And Translation", eds. 1984. Abstract.
Freshney, "Culture Of Animal Cells", Alan R. Liss, Inc., 1987. Abstract.
Roig, "Immobilized Cells And Enzymes", IRL Press, 1986. Abstract.
Perbal, "A Practical Guide To Molecular Cloning; the treatise, Methods In Enzymology", Academic Press, Inc., N.Y. 1984. Abstract.
Miller and Calos, "Gene Transfer Vectors For Mammalian Cells", Cold Spring Harbor Laboratory, eds. 1987. Abstract.
Wu et al., "Methods In Enzymology", vols. 154 and 155, 1987. Abstract.
Mayer and Walker, "Immunochemical Methods In Cell And Molecular Biology", Academic Press, London, eds. 1987. Abstract.
Weir and Blackwell, "Handbook Of Experimental Immunology", vols. I-IV, ed. 1986. Abstract.
Hogan et al., "Manipulating the Mouse Embryo", Cold Spring Harbor Laboratory Press, Cold Spring Harbor, N.Y., 1986. Abstract.
Borrebaeck, "Antibody Engineering", 2nd ed. Oxford Univ. Press, ed. 1995. Abstract.
Rickwood et al., "Protein Engineering, A Practical Approach", IRL Press at Oxford Univ. Press, Oxford, Eng., eds. 1995. Abstract.
Nisonoff, "Molecular Immunology", 2nd ed. Sinauer Associates, Sunderland, MA, 1984. Abstract.
Steward, "Antibodies, Their Structure and Function", Chapman and Hall, New York, N.Y. 1984. Abstract.
Stites et al., "Basic and Clinical Immunology", 8th ed; Appleton & Lange, Norwalk, Conn., eds. 1994. Abstract.
Mishell and Shiigi, "Selected Methods in Cellular Immunology", W.H. Freeman and Co., NY., eds. 1980. Abstract.
Sambrook et al., "Molecular Cloning: A Laboratory Manual", Cold Spring Harbor Press, 2001. Abstract.
Coligan et al., "Current Protocols in Immunology", John Wiley & Sons, New York, 1991. Abstract.
International Search Report and Written Opinion for the International Patent Application No. PCT/US2021/038173, dated Sep. 28, 2021, 21 pages.
Walter E. Kaufmann, Jennifer L. Stallworth, David B. Everman & Steven A. Skinner (2016) Neurobiologically-based treatments in Rett syndrome: opportunities and challenges, Expert Opinion on Orphan Drugs, 4:10, 1043-1055, DOI: 10.1080/21678707.2016.1229181.
Kuzirian, Marissa S, and Suzanne Paradis. "Emerging themes in GABAergic synapse development." Progress in neurobiology vol. 95,1 (2011): 68-87. doi:10.1016/j.pneurobio.2011.07.002.

Garré, J.M., Silva, H.M., Lafaille, J.J. et al. P2X7 receptor inhibition ameliorates dendritic spine pathology and social behavioral deficits in Rett syndrome mice. Nat Commun 11, 1784 (2020).
Lioy et al., "A role for glia in the progression of Rett's syndrome", Nature, 475(7357):497-500, 2012.
Juo, "Concise Dictionary of Biomedicine and Molecular Biology", 2nd ed., CRC Press, 2002. Abstract.
Lackie et al., "The Dictionary of Cell and Molecular Biology", 3rd ed., Academic Press, 1999. Abstract.
Smith et al., "Oxford Dictionary Of Biochemistry And Molecular Biology", Revised, Oxford University Press, 2000. Abstract.
Temudo et al., "Abnormal movements in Rett syndrome are present before the regression period: A case study", Movement Disorders 22(15), 2284-2287, 2007. Abstract.
Einspieler et al., "Is the early development of girls with Rett disorder really normal?", Pediatric Research 57, 696-700, 2005.
Kikutani et al., "A Semaphorins in interactions between T cells and antigen-presenting cells", Nature Rev. Immunol. 3:159-167, 2003. Abstract.
Suzuki et al., "Semaphorins and their receptors in immune cell interactions", Nature Immunol., 9:17-23, 2008. Abstract.
Harlow et al., "Antibodies: A Laboratory Manual", 2nd ed.; Cold Spring Harbor Laboratory Press, 1988. Abstract.
Hamers-Casterman et al., "Naturally occurring antibodies devoid of light chains", Nature 363:446-448, 1993. Abstract.
Kabat et al., "Sequences of Proteins of Immunological Interest", U.S. Dept. of Health and Human Services, 1983. Abstract.
Chothia et al., "Canonical Structures for the Hypervariable Regions of Immunoglobulins", Journal of Molecular Biology 196:901-917, 1987.
Jones et al., "Replacing the Complementarity-Determining Regions in a Human Antibody with those from a Mouse", Nature 321:522-525, 1986.
Riechmann et al., "Reshaping Human Antibodies for Therapy", Nature 332:323-329, 1988. Abstract.
Verhoeyen et al., "Reshaping Human Antibodies: Grafting an Antilysozyme Activity", Science, 239:1534-1536, 1988.
Presta, "Antibody Engineering", Current Opinion in Structural Biology, 2(4):593-596, 1992. Abstract.
Tamagnone et al., "Plexins Are a Large Family of Receptors for Transmembrane, Secreted, and GPI-Anchored Semaphorins in Vertebrates", Cell 99:71-80, 1999.
Giraudon et al., "Semaphorin CD100 from Activated T Lymphocytes Induces Process Extension Collapse in Oligodendrocytes and Death of Immature Neural Cells", The Journal of Immunology, 172:1246-1255, 2004.
Giraudon et al., "T-Cells in Neuonal Injury and Repair", NeuroMolecular Medicine, 7:207-216, 2005. Abstract.
Kruger et al., "Semaphorins command cells to move", Nature Rev. Mol. Cell Biol. 6:789-800, 2005.
Pasterkamp, "R-Ras Fills Another GAP in Semaphorin Signalling", Trends in Cell Biology, 15:61-64, 2005. Abstract.
Azzarelli et al., "An antagonistic interaction between PlexinB2 and Rnd3 controls RhoA activity and cortical neuron migration", Nature Communications, 5:3405, Feb. 27, 2014.
Saha et al., "Plexin-B2 Regulates the Proliferation and Migration of Neuroblasts in the Postnatal and Adult Subventricular Zone", The Journal of Neuroscience, 32(47):16892-16905, Nov. 21, 2012.
Ishida et al., "Involvement of CS100, a Lymphocyte Semaphorin, in the Activation of the Human Immune System via CD72; Implications for the Regulation of Immune and Inflammatory Responses", International Immunololy 15:1027-1034, 2003.
Kumanogoh et al., "The CD100-CD72 interaction: a novel mechanism of immune regulation", Trends in Immunology, 22:670-676, 2001. Abstract.
Elhabazi et al., "Biological Activity of Soluble CD100. I. The Extracellular Region of CD100 Is Released from the Surface of T Lymphocytes by Regulated Proteolysis", The Journal of Immunology, 166:4341-4347, 2001.
Delaire et al., "Biological Activity of Soluble CD100. II. Soluble CD100, Similarly to H-Semalll, Inhibits Immune Cell Migration", J Immunol. 166:4348-4354, 2001.

(56) References Cited

OTHER PUBLICATIONS

Shi et al., "The class IV semaphorin CD100 plays nonredundant roles in the immune system: Defective B and T cell activation in CD100-deficient mice", Immunity 13:633-642, 2000.
Kumanogoh et al., "Requirement for the Lymphocyte Semaphorin, CD100, in the Induction of Antigen-Specific T Cells and the Maturation of Dendritic Cells", The Journal of Immunology, 169:1175-1181, 2002.
Watanabe et al., "Enhanced Immune Responses in Transgenic Mice Expressing a Truncated Form of the Lymphocyte Semaphorin CD100", Journal of Immunology, 167:4321-4328, 2001.
Wang et al., "Functional soluble CD100/Sema4D released from activated lymphocytes: possible role in normal and pathologic immune responses", Blood 97:3498-3504, 2001.
Smith et al., "SEMA4D compromises blood-brain barrier, activates microglia, and inhibits remyelination in neurodegenerative disease", Neurobiology of Disease 73, 254-268, 2015.
Southwell et al., "Anti-semaphorin 4D immunotherapy ameliorates neuropathology and some cognitive impairment in the YAC128 mouse model of Huntington disease", Neurobiology of Disease 76, 46-56, 2015.
Barres, "The Mystery and Magic of Glia: A Perspective on Their Roles in Health and Disease", Neuron 60:430-440, 2008.
Weese-Mayer et al., "Autonomic Nervous System Dysregulation: Breathing and Heart Rate Perturbation During Wakefulness in Young Girls with Rett Syndrome", Pediatric Research 60:443-449, 2006.
Herold et al., "Activation signals are delivered through two distinct epitopes of CD100, a unique 150 kDa human lymphocyte surface structure previously defined by BB18 mAb", Int. Immunol. 7(1): 1-8, 1995.
Walker and Gaastra, Techniques in Molecular Biology (MacMillan Publishing Company, New York); eds. 1983. Abstract.
Kunkel, "Rapid and efficient site-specific mutagenesis without phenotypic selection", Proc. Natl. Acad. Sci. 82:488-492, 1985. Abstract.
Kunkel et al., "Rapid and efficient site-specific mutagenesis without phenotypic selection", Methods Enzymol. 154:367-382, 1987.
Sambrook et al., "Molecular Cloning: A Laboratory Manual", Cold Spring Harbor, N.Y., 1989. Abstract.
Karlin et al., "Applications and statistics for multiple high-scoring segments in molecular sequences", Proc. Natl. Acad. Sci. USA 90(12):5873-5877, 1993. Abstract.
Smith and Waterman, "Comparison of Biosequences", Advances in Applied Mathematics 2:482-489, 1981.
Lewis et al., "Purification, sequence, and cellular localization of a novel chromosomal protein that binds to methylated DNA", Cell. 69 (6): 905-14, Jun. 1992. Abstract.
Luikenhuis et al., "Expression of MeCP2 in postmitotic neurons rescues Rett syndrome in mice", Proc. Natl. Acad. Sci. U.S.A. 101 (16): 6033-8, Apr. 4, 2004.
Chahrour et al., "The Story of Rett Syndrome: From Clinic to Neurobiology", Neuron 56:422-437, 2007.
Guy et al., "A mouse Mecp2-null mutation causes neurological symptoms that mimic Rett syndrome", Nat. Genet. 27:322-326, 2001. Abstract.
Chen et al., "Deficiency of methyl-CpG binding protein-2 in CNS neurons results in a Rett-like phenotype in mice", Nat. Genet. 3:327-331, 2001. Abstract.
McGill et al., "Enhanced anxiety and stress-induced corticosterone release are associated with increased Crh expression in a mouse model of Rett syndrome", Proc. Nat. Acad. Sci. 103: 18267-72, 2006.
Komada et al., "Elevated plus maze for mice", Vis. Exp., Dec. 22 (22):1088, 2008.
Goffin et al., "Rett syndrome mutation MeCP2 T158A disrupts DNA binding, protein stability and ERP responses", Nature Neuroscience 15:274 283, 2012. Abstract.
Dayhoff, M.O., Schwartz, R.M. and Orcutt, B.C. (1978) A model of evolutionary change in proteins, in Dayhoff, M.O. Edition, Atlas of Protein Sequence and Structure. Natl. Biomed. Res. Found., Washington DC, 5(3), 345- 352.
Kumanogoh et al., "Identification of CD72 as a Lymphocyte Receptor for the Class IV Semaphorin CD100: A novel Mechanism for Regulating B Cell Signaling", Immunity 13(5):621-631 (2000).
Kumanogoh et al. "Immune semaphorins: a new area of semaphorin research" J Cell Sci 116(Part 17):3463-3470 (2003).
Sambrook et al., ed. (1992) Molecular Cloning: A Laboratory Manual, (Cold Springs Harbor Laboratory, NY).
Vashi et al., "Treating Rett syndrome: from mouse models to human therapies", Mamm Genome 30(5-6):90-110 (2019). doi: 10.1007/s00335-019-09793-5.

* cited by examiner

Hindlimb Clasping Scoring Criteria

Inspiratory Time

Expiratory Time

Control (C57/BL6)

SEMA4D

Mecp2$^{T158A}$

SEMA4D

HuC/HuD neuronal marker

HuC/HuD neuronal marker

USE OF SEMAPHORIN-4D BINDING MOLECULES FOR THE TREATMENT OF RETT SYNDROME

SEQUENCE LISTING

The instant application contains a Sequence Listing which has been submitted electronically in ASCII format and is hereby incorporated by reference in its entirety. Said ASCII copy, created on Jun. 24, 2020, is named 8555_039Z_SL.txt and is 29,049 bytes in size.

BACKGROUND OF THE DISCLOSURE

Rett syndrome (RTT) is a neurodevelopmental disorder that is mostly caused by mutations in the X-linked gene Methyl CpG-binding Protein 2 (MECP2). Rett syndrome predominantly affects girls and is the second most common cause of severe intellectual disability after Down syndrome, with an incident of 1:10,000 live births. Patients suffer from cognitive and physical disabilities, with most of them wheel chair bound and requiring full time care. There is no cure to date, however, the late onset from 6-18 months of life provides a valuable window of opportunity for therapeutic intervention. An experimental model, Mecp2-deficient mice, is available for preclinical research. A significant contribution to research in RTT is the proof of concept demonstration that re-expression of MeCP2 in Mecp2-deficient mice, preferentially in astrocytes, significantly improved locomotion and anxiety levels, restored respiratory abnormalities to a normal pattern, and greatly prolonged lifespan compared to globally null mice. These studies showed that glia, like neurons, are integral components of the neuropathology of RTT. (Lioy et al., Nature, 475(7357):497-500 (2012)) This landmark achievement, whereby Mecp2 expression was restored in the mutant mice, leading to a dramatic recovery from their "Rett-like phenotype," has increased the motivation to find a cure. However, there remains a need for treatments for Rett syndrome that alleviate the symptoms associated with the disorder.

BRIEF SUMMARY OF THE DISCLOSURE

Methods for using semaphorin 4D (SEMA4D) binding molecules to alleviate symptoms in a subject with Rett syndrome are disclosed herein. According to aspects of the disclosure illustrated herein, there is provided a method for improving symptoms in a subject with Rett syndrome including administering to the subject an effective amount of an isolated binding molecule which specifically binds to SEMA4D and inhibits, suppresses, prevents, reverses or slows the effect of SEMA4D on disease progression.

According to aspects illustrated herein, there is provided a method of treating a subject with Rett syndrome including administering to the subject an effective amount of an isolated binding molecule which specifically binds to SEMA4D, wherein the binding to SEMA4D acts to improve symptoms associated with the disorder.

Methods of alleviating symptoms in a subject having Rett syndrome are provided, comprising administering to that subject an effective amount of an isolated binding molecule which specifically binds to SEMA4D. In certain embodiments of the methods, the binding molecule inhibits SEMA4D interaction with its receptor or a portion of its receptor. In certain embodiments of the methods, the receptor is selected from the group consisting of Plexin-B1, Plexin-B2 and CD72. In certain embodiments of the methods, the binding molecule inhibits SEMA4D-mediated Plexin-B1 signal transduction. In certain embodiments of the methods, the isolated binding molecule specifically binds to the same SEMA4D epitope as a reference monoclonal antibody selected from the group consisting of VX15/2503, Mab D2517, D2585, and MAb 67. In certain embodiments of the methods, the isolated binding molecule competitively inhibits a reference monoclonal antibody selected from the group consisting of VX15/2503, Mab D2517, D285, and MAb 67 from specifically binding to SEMA4D. In certain embodiments of the methods, the isolated binding molecule comprises an antibody or antigen-binding fragment thereof. In certain embodiments of the methods, the antibody or antigen-binding fragment thereof is monoclonal antibody VX15/2503 or MAb 67. In certain embodiments of the methods, the antibody or antigen-binding fragment thereof comprises a variable heavy chain (VH) comprising VHCDRs 1-3 comprising SEQ ID NOs 3, 4, and 5, respectively, and a variable light chain (VL) comprising VLCDRs 1-3 comprising SEQ ID NOs 8, 9, and 10, respectively. In certain embodiments of the methods, the VH and VL comprise, respectively, SEQ ID NO: 6 and SEQ ID NO: 11, SEQ ID NO: 7 and SEQ ID NO: 12, or SEQ ID NO: 21 and SEQ ID NO: 25. In certain embodiments of the methods, the antibody or antigen-binding fragment thereof comprises a variable heavy chain comprising VHCDRs 1-3 comprising SEQ ID NO: 22, SEQ ID NO: 23, and SEQ ID NO: 24, respectively, and a variable light chain comprising VLCDRs1-3 comprising SEQ ID NO: 26, SEQ ID NO: 27, and SEQ ID NO: 28, respectively.

In certain embodiments of any one of the aforementioned methods, the symptoms treated are selected from a group consisting of neuropsychiatric symptoms, cognitive symptoms, motor dysfunction, and any combination thereof. In certain embodiments of any of the aforementioned methods, the subject has stage I Rett syndrome. In certain embodiments, alleviation of the neuropsychiatric symptoms includes reducing anxiety-like behavior, decreasing sleep disturbances, reducing agitation, reducing restlessness, and any combination thereof. In certain embodiments, the symptoms that are alleviated are selected from the group consisting of neuropsychiatric symptoms, cognitive symptoms, delayed physical development, delayed communication development, loss of communication skills, motor dysfunction, sleep disturbances, irregular heartbeat, repetitive jerky movements, body tremors, and any combination thereof. In certain embodiments, alleviating symptoms comprises preventing or reducing anxiety-like behavior, increasing cognition, increasing coordination, increasing locomotion, progressing physical development, decreasing body tremors, decreasing repetitive movements, increasing motor skills, increasing communication skills, decreasing sleep disturbances, decreasing agitation, decreasing restlessness, and any combination thereof.

In certain embodiments, the subject is in Stage II, Stage III, or Stage IV of Rett syndrome. In certain embodiments, the Stage II, Stage III, or Stage IV subject exhibits symptoms selected from the group consisting of neuropsychiatric symptoms, cognitive symptoms, delayed physical development, motor dysfunction, irregular heartbeat and breathing, decreased communication skills, scoliosis, sleep disturbances, seizures, gastrointestinal problems, repetitive jerky motions, body tremors, and any combination thereof. In certain embodiments, the alleviation of symptoms includes reducing anxiety-like behavior, increasing cognition, increasing coordination, increasing locomotion, progressing physical development, decreasing body tremors, decreasing repetitive motions, increasing motor skills, increasing communication skills, decreasing sleep disturbances, decreasing agitation, decreasing restlessness, or any combination thereof.

BRIEF DESCRIPTION OF THE DRAWINGS/FIGURES

Figure 4A:
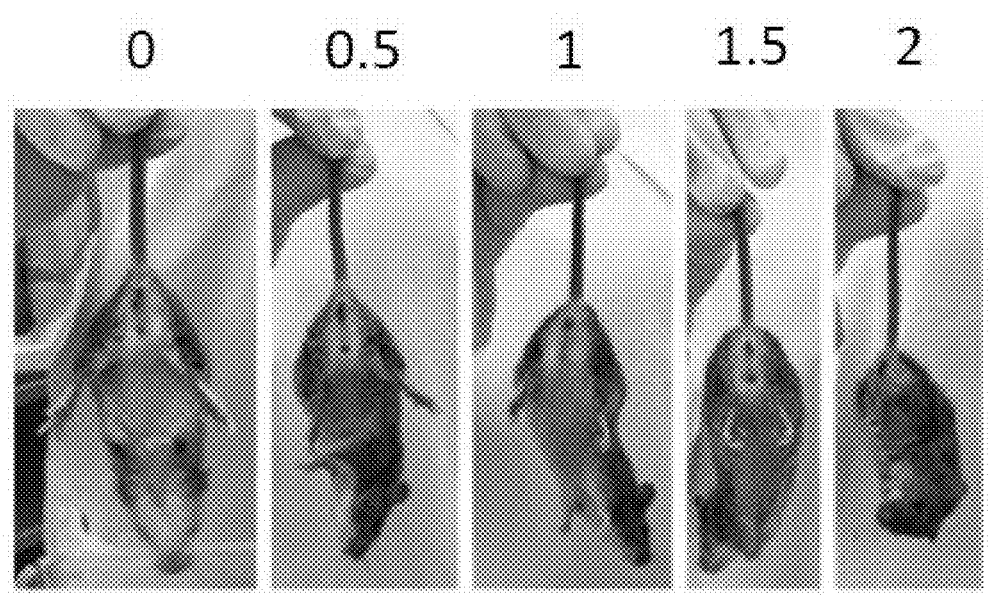
Figure 4B:
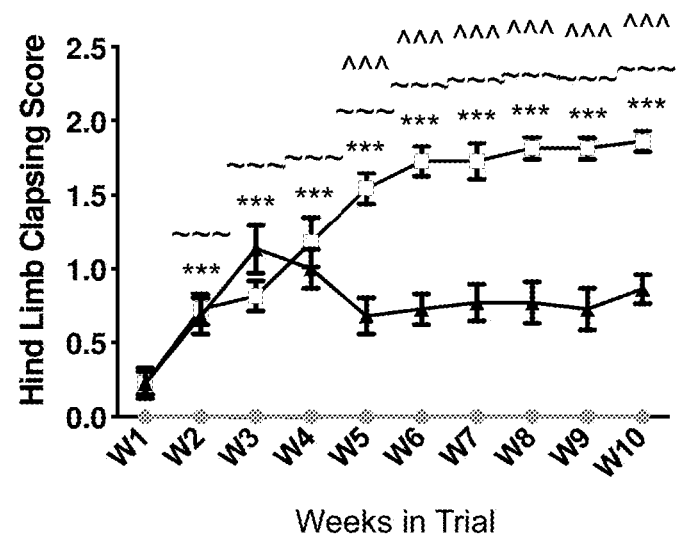

FIG. 4A demonstrates hindlimb clasping in Mecp2 mice on a scale of 0 (no clasping) to 2 (most severe). FIG. 4B shows the degree of hindlimb clasping in 4-week old wild type mice treated with control antibody (-●- WT), 4-week old (pre-symptomatic) Mecp2 mice treated with control antibody (-■- P), and 4-week old (pre-symptomatic) MeCP2 mice treated with anti-SEMA4D antibody (-▲- T). * WT vs P, ~ WT vs T, ˆ P vs T. (WT=wild type mice treated with control antibody; P=Rett mice treated with control antibody; T=Rett mice treated with anti-SEMA4D antibody). *, ~, and ˆ $p \leq 0.05$; ~~, and ˆˆ $p \leq 0.01$; and *, ~~~, and ˆˆˆ $p \leq 0.001$.

Figure 5:
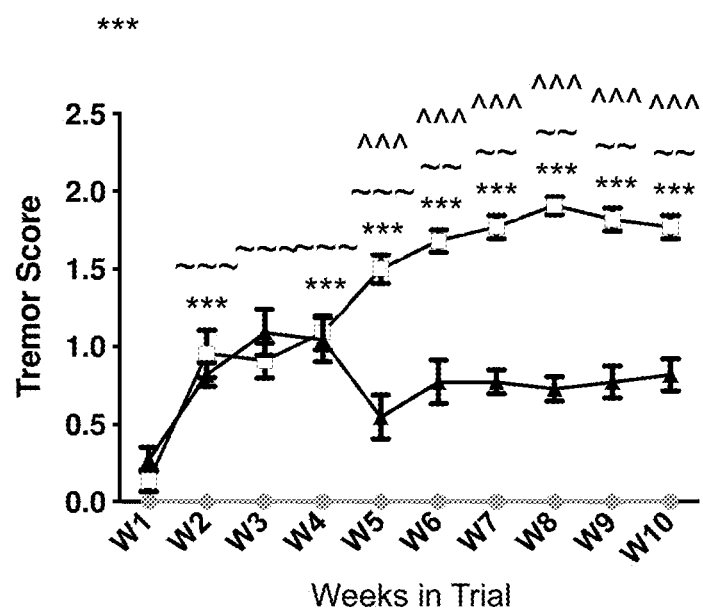

FIG. 5 graphically demonstrates whole body tremors exhibited by age-matched wild type mice treated with control antibody (-●- WT), pre-symptomatic Mecp2 mice treated with control antibody (-■- P) and pre-symptomatic Mecp2 mice treated with anti-SEMA4D antibody (-▲- T). * WT vs P, ~ WT vs T, ˆ P vs T. (WT=wild type mice treated with control antibody; P=Rett mice treated with control antibody; T=Rett mice treated with anti-SEMA4D antibody).*, ~, and ˆ $p \leq 0.05$; , ~~, and ˆˆ $p \leq 0.01$; and *, ~~~, and ˆˆˆ $p \leq 0.001$.

Figure 6:
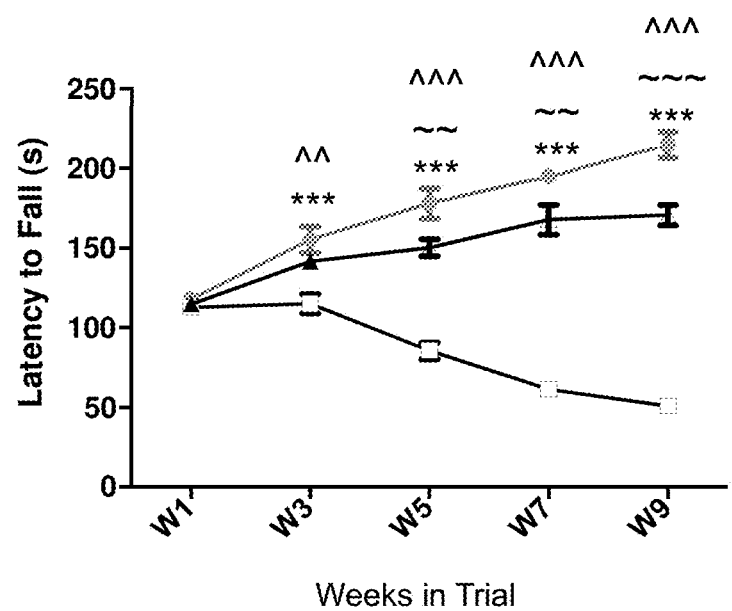

FIG. 6 graphically demonstrates the results of locomotion and coordination skills testing of age-matched pre-symptomatic and wild type mice on an accelerating rotarod apparatus over a ten week period: 4-week old wild type mice treated with control antibody (-●- WT), 4-week old (pre-symptomatic) Mecp2 mice treated with control antibody (-■- P), and 4-week old (pre-symptomatic) Mecp2 mice treated with anti-SEMA4D antibody (-▲- T). * WT vs P, ~ WT vs T, ˆ P vs T. (WT=wild type mice treated with control antibody; P=Rett mice treated with control antibody; T=Rett mice treated with anti-SEMA4D antibody). *, ~, and ˆ $p \leq 0.05$; , ~~, and ˆˆ $p \leq 0.01$; and *, ~~~, and ˆˆˆ $p \leq 0.001$.

Figure 7A:
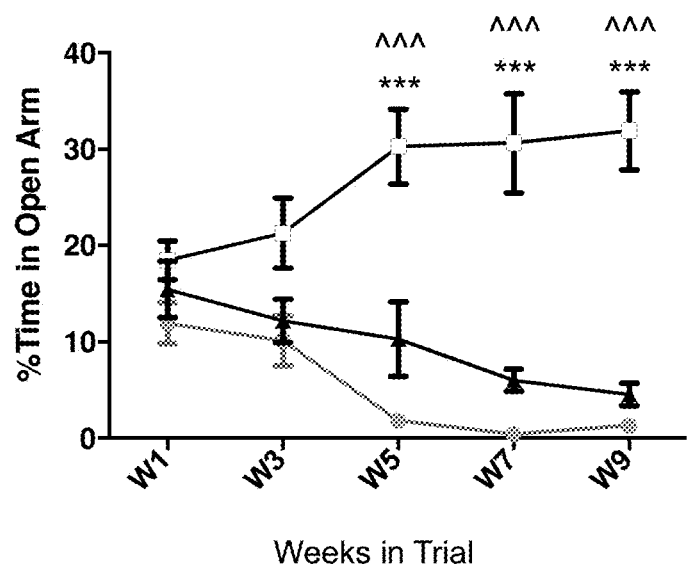
Figure 7B:
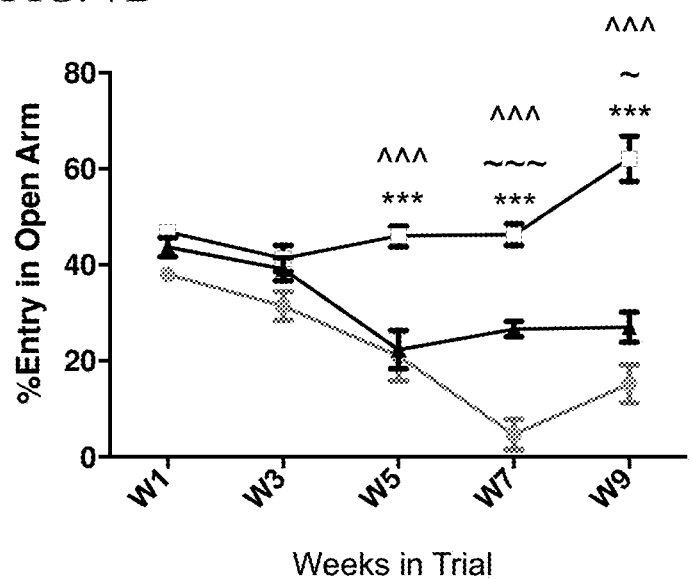

FIG. 7 graphically demonstrates the results of cognition testing of age matched pre-symptomatic Mecp2 and wild type mice using an elevated plus maze (EPM) apparatus over a ten week period. FIG. 7A shows percentage amount of time spent in the open arm area of the apparatus; FIG. 7B shows the percentage of entries into the open arm area of the apparatus: 4-week old wild type mice treated with control antibody (-●- WT), 4-week old (pre-symptomatic) Mecp2 mice treated with control antibody (-■- P) and 4-week old (pre-symptomatic) Mecp2 mice treated with anti-SEMA4D antibody (-▲- T). * WT vs P, ~WT vs T, ˆ P vs T. (WT=wild type mice treated with control antibody; P=Rett mice treated with control antibody; T=Rett mice treated with anti-SEMA4D antibody). *, ~, and ˆ $p \leq 0.05$; , ~~, and ˆˆ $p \leq 0.01$; and *, ~~~, and ˆˆˆ $p \leq 0.001$.

Figure 8A:
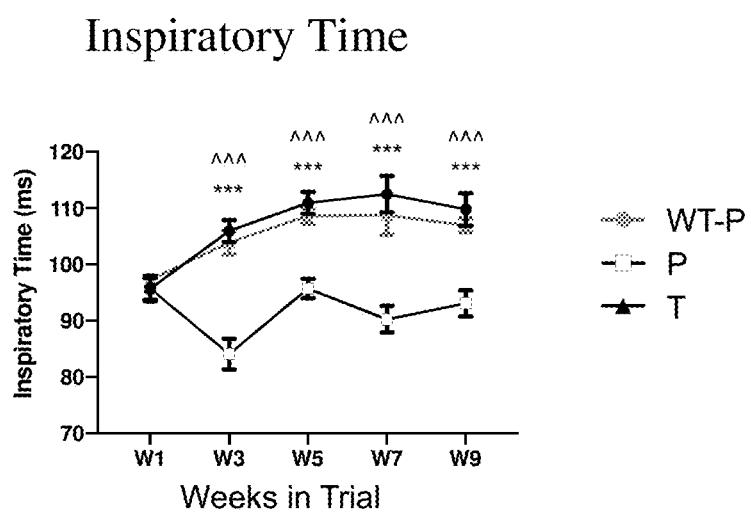
Figure 8:
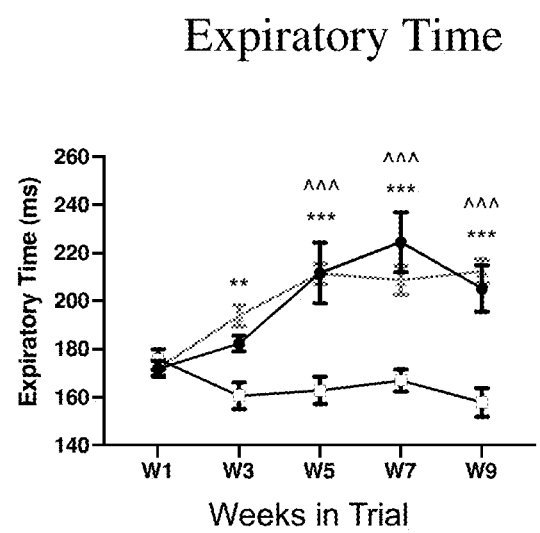

FIG. 8 graphically shows the results of whole body plethysmography testing of age matched wild type and Mecp2 mice over a nine week period. FIG. 8A shows the inspiratory period; FIG. 8B shows the expiratory period: 4-week old wild type mice treated with control antibody (-●- WT), 4-week old (pre-symptomatic) Mecp2 mice treated with control antibody (-■- P) and 4-week old (pre-symptomatic) Mecp2 mice treated with anti-SEMA4D antibody (-▲- T). * WT vs P, ~WT vs T, ˆ P vs T. (WT=wild type mice treated with control antibody; P=Rett mice treated with control antibody; T=Rett mice treated with anti-SEMA4D antibody). *, ~, and ˆ $p \leq 0.05$; , ~~, and ˆˆ $p \leq 0.01$; and *, ~~~, and ˆˆˆ $p \leq 0.001$.

Figure 9:
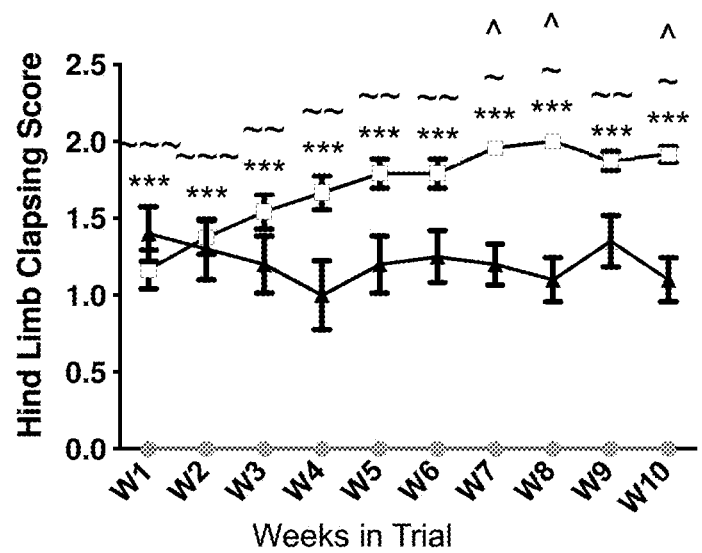

FIG. 9 graphically shows the of hindlimb clasping in 8-week old wild type mice treated with control antibody (-●- WT), 8-week old (pre-symptomatic) Mecp2 mice treated with control antibody (-■- P), and 8-week old (pre-symptomatic) Mecp2 mice treated with anti-SEMA4D antibody (-▲- T). * WT vs P, ~WT vs T, ˆ P vs T. (WT=wild type mice treated with control antibody; P=Rett mice treated with control antibody; T=Rett mice treated with anti-SEMA4D antibody). *, ~, and ˆ $p \leq 0.05$; , ~~, and ˆˆ $p \leq 0.01$; and *, ~~~, and ˆˆˆ $p \leq 0.001$.

Figure 10:
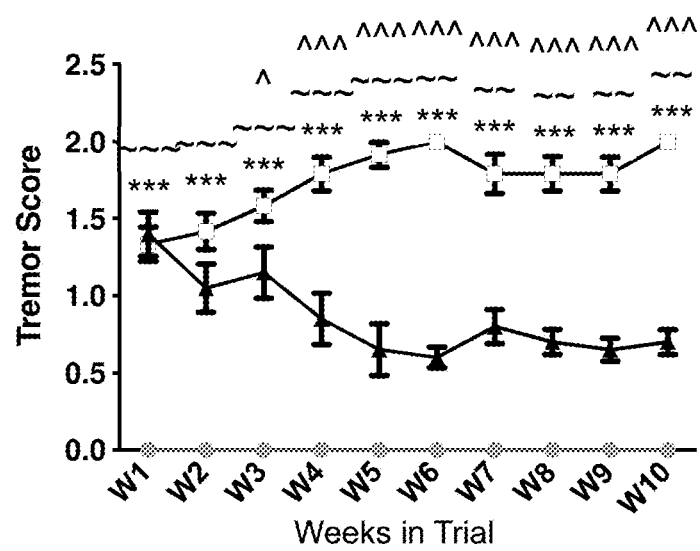

FIG. 10 graphically demonstrates whole body tremors exhibited by age matched wild type mice treated with control antibody (-●- WT), 8-week old symptomatic Mecp2 mice treated with control antibody (-■- P), and symptomatic Mecp2 mice treated with anti-SEMA4D antibody (-▲- T). * WT vs P, ~WT vs T, ˆ P vs T. (WT=wild type mice treated with control antibody; P=Rett mice treated with control antibody; T=Rett mice treated with anti-SEMA4D antibody). *, ~, and ˆ $p \leq 0.05$; , ~~, and ˆˆ $p \leq 0.01$; and *, ~~~, and ˆˆˆ $p \leq 0.001$.

Figure 11:
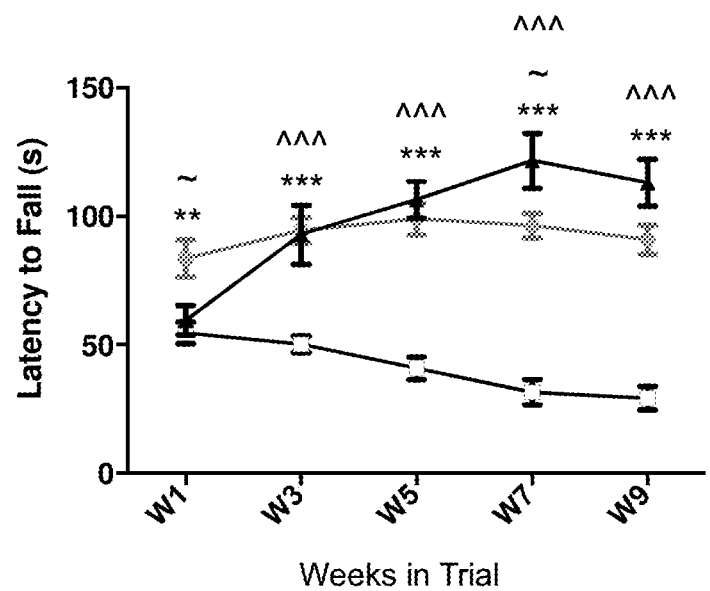

FIG. 11 graphically demonstrates the results of locomotion and coordination skills testing of age-matched symptomatic and wild type mice on an accelerating rotarod apparatus over a ten week period: 8-week old wild type mice treated with control antibody (-●- WT), 8-week old (symptomatic) Mecp2 mice treated with control antibody (-■- P), and 8-week old (symptomatic) Mecp2 mice treated with anti-SEMA4D antibody (-▲- T). * WT vs P, ~WT vs T, ˆ P vs T. (WT=wild type mice treated with control antibody; P=Rett mice treated with control antibody; T=Rett mice treated with anti-SEMA4D antibody). *, ~, and ˆ $p \leq 0.05$; , ~~, and ˆˆ $p \leq 0.01$; and *, ~~~, and ˆˆˆ $p \leq 0.001$.

Figure 12A:
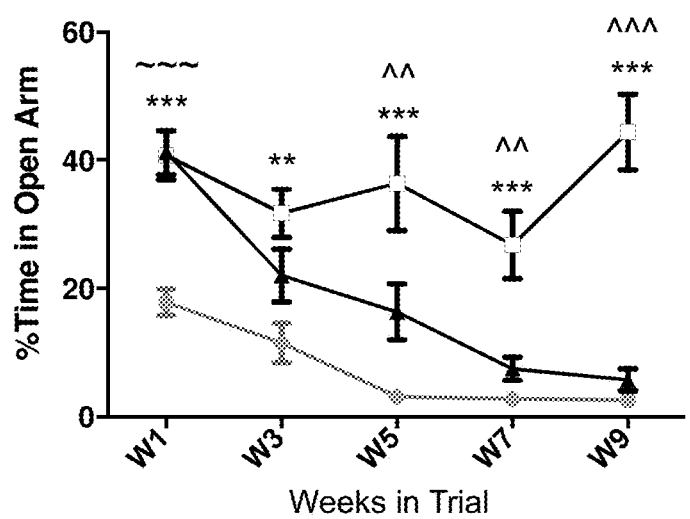
Figure 12B:
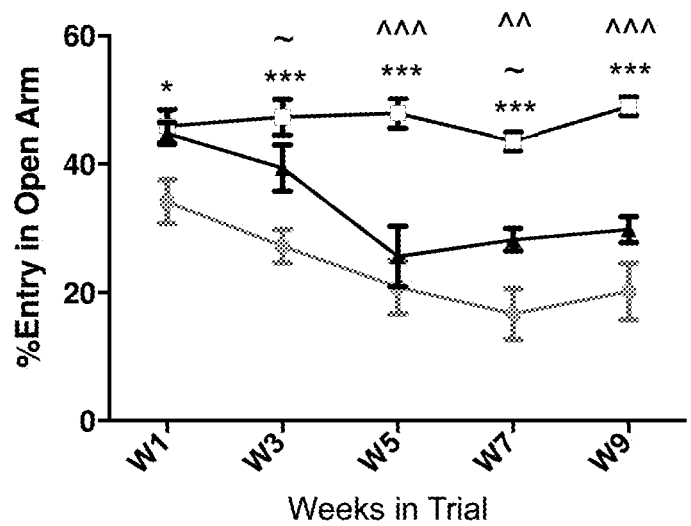

FIG. 12 graphically demonstrates the results of cognition testing of age matched symptomatic MeCP2 and wild type mice using an elevated plus maze (EPM) apparatus over a ten week period. FIG. 12A shows percentage amount of time spent in the open arm area of the apparatus; FIG. 12B shows the percentage of entries into the open arm area of the apparatus: 8-week old wild type mice treated with control antibody (-●- WT), 8-week old (symptomatic) MeCP2 mice treated with control antibody (-■- P), and 8-week old (pre-symptomatic) MeCP2 mice treated with anti-SEMA4D antibody (-▲- T). * WT vs P, ~WT vs T, ˆ P vs T. (WT=wild type mice treated with control antibody; P=Rett mice treated with control antibody; T=Rett mice treated with anti-SEMA4D antibody). *, ~, and ˆ $p \leq 0.05$; , ~~, and ˆˆ $p \leq 0.01$; and *, ~~~, and ˆˆˆ $p \leq 0.001$.

Figure 13A:
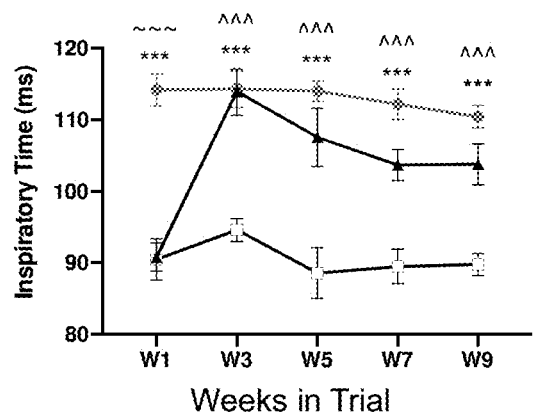
Figure 13B:
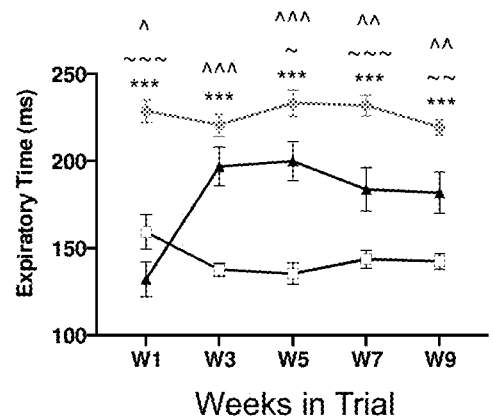

FIG. 13 graphically shows the results of whole body plethysmography testing of age matched wild type and Mecp2 mice over a nine week period. FIG. 13A shows the inspiratory period; FIG. 13B shows the expiratory period: 8-week old wild type mice treated with control antibody (-●- WT), 8-week old (pre-symptomatic) Mecp2 mice treated with control antibody (-■- P), and 8-week old (pre-symptomatic) Mecp2 mice treated with anti-SEMA4D antibody (-▲- T). * WT vs P, ~WT vs T, ˆ P vs T. (WT=wild type mice treated with control antibody; P=Rett mice treated with control antibody; T=Rett mice treated with anti-SEMA4D antibody). *, ~, and ˆ p≤0.05; , ~~, and ˆˆ p≤0.01; and *, ~~~, and ˆˆˆ p≤0.001.

Figure 14A:
Figure 14C:
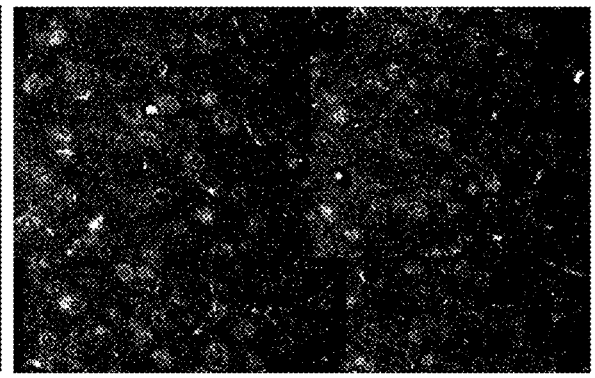
Figure 14B:
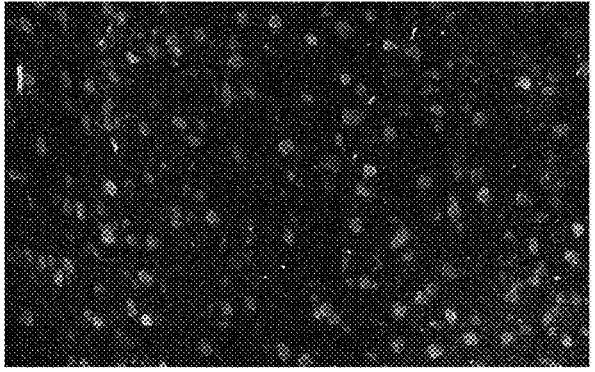
Figure 14:
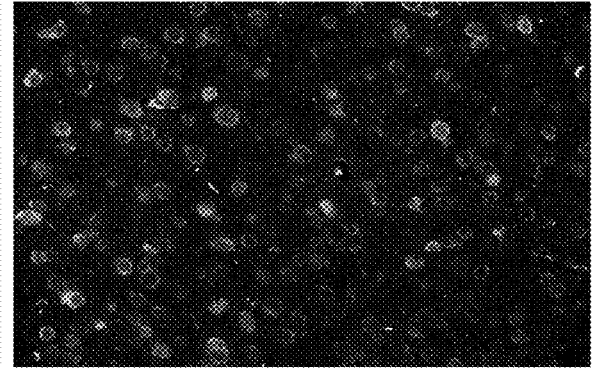

FIG. 14 shows formalin fixed paraffin embedded sections of brains from ~8 month old female mice (Mecp2$^{T158A}$ and wild type littermate controls C57/BL6) that were stained for SEMA4D (CD100 Polyclonal Antibody-Invitrogen-PA5-47711) and neuronal marker HuC/HuD (HuC/HuD Monoclonal Antibody (16A11)-Invitrogen: A-21271). Representative images of hippocampus regions are shown. FIG. 14 A: C57/BL6mice stained for SEMA4D; FIG. 14B: C57/BL6mice stained for HuC/HuD; FIG. 14 C: Mecp2$^{T158A}$ mice stained for SEMA4D; and FIG. 14 D: Mecp2$^{T158A}$ mice stained for HuC/HuD.

DETAILED DESCRIPTION OF THE DISCLOSURE

I. Definitions

It is to be noted that the term "a" or "an" entity refers to one or more of that entity; for example, "an anti-SEMA4D antibody" is understood to represent one or more anti-SEMA4D antibodies. As such, the terms "a" (or "an"), "one or more," and "at least one" can be used interchangeably herein.

Furthermore, "and/or" where used herein is to be taken as specific disclosure of each of the two specified features or components with or without the other. Thus, the term and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

Unless defined otherwise, technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Systeme International de Unites (SI) accepted form. Numeric ranges are inclusive of the numbers defining the range. Unless otherwise indicated, amino acid sequences are written left to right in amino to carboxy orientation. The headings provided herein are not limitations of the various aspects or aspects of the disclosure, which can be had by reference to the specification as a whole. Accordingly, the terms defined immediately below are more fully defined by reference to the specification in its entirety.

As used herein, the term "non-naturally occurring" substance, composition, entity, and/or any combination of substances, compositions, or entities, or any grammatical variants thereof, is a conditional term that explicitly excludes, but only excludes, those forms of the substance, composition, entity, and/or any combination of substances, compositions, or entities that are well-understood by persons of ordinary skill in the art as being "naturally-occurring," or that are, or might be at any time, determined or interpreted by a judge or an administrative or judicial body to be, "naturally-occurring."

As used herein, the term "neurodevelopmental disorder" refers to impairments of the growth and development of the brain or central nervous system. The term refers to a disorder of brain function that affects emotion, learning ability, self-control, motor control and memory and that unfolds as the individual grows, i.e., the course of the disorder changes over time. Rett syndrome is a rare genetic neurological and developmental disorder (an X-linked neurodevelopmental disorder) that affects the way the brain develops, causing a progressive loss of motor skills and speech.

As used herein, the term "Rett syndrome" (RTT) refers to a progressive disease initially manifesting at about six to eighteen months of age in a human followed first by a period of stagnation and then by rapid regression in motor and language skills. Rett syndrome affects nearly every aspect of the child's life: their ability to speak, walk, eat, and even breathe easily. Symptoms include problems with language, coordination, and repetitive movements. Often there is slower growth, loss of normal movement and coordination, loss of communication abilities, unusual eye movements, e.g., intense staring, blinking, crossed eyes or closing one eye at a time, breathing problems, irritability, cognitive disabilities, irregular heartbeat, and a smaller than normal head size. Complications can include seizures, scoliosis, and sleeping problems, as well as breathing issues. The hallmark of Rett syndrome is near constant repetitive hand movements. Those affected, however, may be affected to different degrees. In general, the disorder unfolds in a sequence of four "stages" which encapsulate specific changes in subjects as the disorder progresses. Subjects (primarily girls) with classic RTT have an apparently normal period of normal development, and at about 6-18 months of age the early signs of the disorder emerge. In Stage 1 of the disorder stagnation and/or delay in development occurs, and the subject stops meeting the expected developmental milestones. This is followed by Stage II, the rapid regression period where subjects, between the age of 1 and 4, lose acquired skills such as communication and socialization, as well as losing some fine and gross motor skills. In addition, deceleration of head growth may occur. It is during this period that stereotypic hand movements, a hallmark of RTT, become apparent. (Temudo, et al. (2007) Abnormal movements in Rett syndrome are present before the regression period: a case study. Mov. Disord. 22, 2284-2287; Einspieler et al. (2005) Is the early development of girls with Rett disorder really normal? Pediatr. Res. 57, 696-700.) Stage III is a post-regression stage, where the phenotype stabilizes. During this period many subjects develop an intense eye gaze and increased social awareness. They may also partially regain some of the skills lost during Stage II. The last stage, Stage IV, is the late motor deterioration stage and can last for years to decades. This stage is characterized by reduced mobility, muscle weakness, rigidity, and spasticity, with the development of dystonia and hand and foot deformities as the subject grows older. Walking may cease but eye gaze usually improves, repetitive hand movements may decrease, and cognition, communication, or hand skills generally do not decline.

The term "therapeutically effective amount" refers to an amount of an antibody, polypeptide, polynucleotide, small organic molecule, or other drug effective to "treat" a disease or disorder in a subject or mammal. In the case of a neurodevelopmental disorder, the therapeutically effective amount of the drug can alleviate symptoms of the disorder;

decrease, reduce, retard or stop the incidence of symptoms; decrease, reduce, retard the severity of symptoms; inhibit, e.g., suppress, retard, prevent, stop, or reverse the manifestation of symptoms; relieve to some extent one or more of the symptoms associated with the disorder; reduce morbidity and mortality; improve quality of life; or a combination of such effects.

The term "symptoms" as referred to herein refer to, e.g., 1) neuropsychiatric symptoms, 2) cognitive symptoms, and 3) motor dysfunction. Examples of neuropsychiatric symptoms include, for instance, anxiety-like behavior, sleep disturbances, and irritability. Examples of cognitive symptoms include, for instance, learning and memory deficits. Examples of motor dysfunction include, for instance, locomotion or coordination difficulties or repetitive movements, e.g., hand movements such as hand wringing.

Terms such as "treating" or "treatment" or "to treat" or "alleviating" or "to alleviate" or "improving" or "to improve" refer to both 1) therapeutic measures that cure, slow down, lessen symptoms of, reverse, and/or halt progression of a diagnosed pathologic condition or disorder and 2) prophylactic or preventative measures that prevent and/or slow the development of a targeted pathologic condition or disorder. Thus, those in need of treatment include those already with the disorder; those prone to have the disorder; and those in whom the disorder is to be prevented. Beneficial or desired clinical results include, but are not limited to, alleviation of symptoms, diminishment of extent of disease, stabilization (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already exhibiting symptoms of the condition or disorder as well as asymptomatic subjects.

Semaphorin 4D (SEMA4D), also known as CD100, is a transmembrane protein (e.g., SEQ ID NO: 1 (human); SEQ ID NO: 2 (murine)) that belongs to the semaphorin gene family. SEMA4D is expressed on the cell surface as a homodimer, but upon cell activation SEMA4D can be released from the cell surface via proteolytic cleavage to generate sSEMA4D, a soluble form of the protein, which is also biologically active. See Suzuki et al., Nature Rev. Immunol. 3:159-167 (2003); Kikutani et al., Nature Immunol. 9:17-23 (2008). SEMA4D is expressed at high levels in lymphoid organs, including the spleen, thymus, and lymph nodes, and in non-lymphoid organs, such as the brain, heart, and kidney. SEMA4D plays an important role as an axonal guidance protein in nervous system development and has been implicated in the development of neurodegenerative disorders, autoimmune diseases, demyelinating diseases, and certain cancers. However, the effect of blocking SEMA4D signalling on the organization and function of the central nervous system (CNS) including brain and spinal cord and on behaviours controlled by the CNS remains to be elucidated. This is important because changes in the CNS have a profound influence on a subject's behaviour and quality of life. In particular, such changes can impact a subject's neuropsychiatric behaviour, cognitive behaviour, and motor skills.

By "subject" or "individual" or "animal" or "patient" or "mammal," is meant any subject, particularly a mammalian subject, e.g., humans, for whom diagnosis, prognosis, or therapy is desired.

As used herein, phrases such as "a subject that would benefit from administration of an anti-SEMA4D antibody" and "an animal in need of treatment" includes subjects, such as mammalian subjects, that would benefit from administration of an anti-SEMA4D antibody or other SEMA4D binding molecule used, e.g., for detection of a SEMA4D polypeptide (e.g., for a diagnostic procedure) and/or from treatment, i.e., palliation or prevention of developing symptoms of Rett syndrome.

A "binding molecule" or "antigen binding molecule" of the present disclosure refers in its broadest sense to a molecule that specifically binds an antigenic determinant. In one embodiment, the binding molecule specifically binds to SEMA4D, e.g., to a transmembrane SEMA4D polypeptide of about 150 kDa or a soluble SEMA4D polypeptide of about 120 kDa (commonly referred to as sSEMA4D). In another embodiment, a binding molecule of the disclosure is an antibody or an antigen binding fragment thereof. In another embodiment, a binding molecule of the disclosure comprises at least one heavy or light chain CDR of an antibody molecule. In another embodiment, a binding molecule of the disclosure comprises at least two CDRs from one or more antibody molecules. In another embodiment, a binding molecule of the disclosure comprises at least three CDRs from one or more antibody molecules. In another embodiment, a binding molecule of the disclosure comprises at least four CDRs from one or more antibody molecules. In another embodiment, a binding molecule of the disclosure comprises at least five CDRs from one or more antibody molecules. In another embodiment, a binding molecule of the disclosure comprises at least six CDRs from one or more antibody molecules.

The present disclosure is directed to a method of alleviating symptoms in a subject having the neurodevelopmental disorder known as Rett syndrome, comprising administering to the subject an anti-SEMA4D binding molecule, e.g., an antibody, or antigen-binding fragment, variant, or derivative thereof. Unless specifically referring to full-sized antibodies such as naturally occurring antibodies, the term"anti-SEMA4D antibody" encompasses full-sized antibodies as well as antigen-binding fragments, variants, analogues, or derivatives of such antibodies, e.g., naturally occurring antibody or immunoglobulin molecules or engineered antibody molecules or fragments that bind antigen in a manner similar to antibody molecules.

As used herein, "human" or "fully human" antibodies include antibodies having the amino acid sequence of a human immunoglobulin and include antibodies isolated from human immunoglobulin libraries or from animals transgenic for one or more human immunoglobulins and that do not express endogenous immunoglobulins, as described infra and, for example, in U.S. Pat. No. 5,939,598 by Kucherlapati et al. "Human" or "fully human" antibodies also include antibodies comprising at least the variable domain of a heavy chain, or at least the variable domains of a heavy chain and a light chain, where the variable domain(s) have the amino acid sequence of human immunoglobulin variable domain(s).

"Human" or "fully human" antibodies also include "human" or "fully human" antibodies, as described above, that comprise, consist essentially of, or consist of, variants (including derivatives) of antibody molecules (e.g., the VH regions and/or VL regions) described herein, which antibodies or fragments thereof immunospecifically bind to a SEMA4D polypeptide or fragment or variant thereof. Standard techniques known to those of skill in the art can be used to introduce mutations in the nucleotide sequence encoding a human anti-SEMA4D antibody, including, but not limited to, site-directed mutagenesis and PCR-mediated mutagenesis which result in amino acid substitutions. In some embodiments, the variants (including derivatives) encode less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference VH region, VHCDR1, VHCDR2, VHCDR3, VL region, VLCDR1, VLCDR2, or VLCDR3.

In certain embodiments, the amino acid substitutions are conservative amino acid substitutions, discussed further below. Alternatively, mutations can be introduced randomly along all or part of the coding sequence, such as by saturation mutagenesis, and the resultant mutants can be screened for biological activity to identify mutants that retain activity (e.g., the ability to bind a SEMA4D polypeptide, e.g., human, murine, or both human and murine SEMA4D). Such variants (or derivatives thereof) of "human" or "fully human" antibodies can also be referred to as human or fully human antibodies that are "optimized" or "optimized for antigen binding" and include antibodies that have improved affinity to antigen.

The terms "antibody" and "immunoglobulin" are used interchangeably herein. An antibody or immunoglobulin comprises at least the variable domain of a heavy chain, and normally comprises at least the variable domains of a heavy chain and a light chain. Basic immunoglobulin structures in vertebrate systems are relatively well understood. See, e.g., Harlow et al. (1988) Antibodies: A Laboratory Manual (2nd ed.; Cold Spring Harbor Laboratory Press).

As used herein, the term "immunoglobulin" comprises various broad classes of polypeptides that can be distinguished biochemically. Those skilled in the art will appreciate that heavy chains are classified as gamma, mu, alpha, delta, or epsilon, ($\gamma$, $\alpha$, $\delta$, $\epsilon$) with some subclasses among them (e.g., $\gamma$1-$\gamma$4 $\gamma$4.$\gamma$4). It is the nature of this chain that determines the "class" of the antibody as IgG, IgM, IgA IgG, or IgE, respectively. The immunoglobulin subclasses (isotypes) e.g., IgG1, IgG2, IgG3, IgG4, IgA1, IgA2, etc. are well characterized and are known to confer functional specialization. Modified versions of each of these classes and isotypes are readily discernible to the skilled artisan in view of the instant disclosure and, accordingly, are within the scope of the instant disclosure. All immunoglobulin classes are clearly within the scope of the present disclosure, the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region.

Light chains are classified as either kappa or lambda (K, $\lambda$) Each heavy chain class can be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light (VL or VK) and heavy (VH) chain portions determine antigen recognition and specificity. Conversely, the constant domains of the light chain (CL) and the heavy chain (typically CH1, CH2 or CH3) confer important biological properties such as secretion, transplacental mobility, Fc receptor binding, complement binding, and the like. By convention the numbering of the constant region domains increases as they become more distal from the antigen binding site or amino-terminus of the antibody. The N-terminal portion is a variable region and at the C-terminal portion is a constant region; the CH3 and CL domains typically comprise the carboxy-terminus of the heavy and light chain, respectively.

As indicated above, the variable region allows the antibody to selectively recognize and specifically bind epitopes on antigens. That is, the VL domain and VH domain, or subset of the complementarity determining regions (CDRs) within these variable domains, of an antibody combine to form the variable region that defines a three dimensional antigen binding site. This quaternary antibody structure forms the antigen binding site present at the end of each arm of the Y. More specifically, the antigen binding site is defined by three CDRs on each of the VH and VL chains. In some instances, e.g., certain immunoglobulin molecules derived from camelid species or engineered based on camelid immunoglobulins, a complete immunoglobulin molecule can consist of heavy chains only, with no light chains. See, e.g., Hamers-Casterman et al., Nature 363:446-448 (1993).

In naturally occurring antibodies, the six "complementarity determining regions" or "CDRs" present in each antigen binding domain are short, non-contiguous sequences of amino acids that are specifically positioned to form the antigen binding domain as the antibody assumes its three dimensional configuration in an aqueous environment. The remainder of the amino acids in the antigen binding domains, referred to as "framework" regions, show less inter-molecular variability. The framework regions largely adopt a $\beta$-sheet conformation and the CDRs form loops that connect, and in some cases form part of, the $\beta$-sheet structure. Thus, framework regions act to form a scaffold that provides for positioning the CDRs in correct orientation by inter-chain, non-covalent interactions. The antigen binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable domain by one of ordinary skill in the art, since they have been precisely defined (see below).

In the case where there are two or more definitions of a term that is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al. (1983) U.S. Dept. of Health and Human Services, "Sequences of Proteins of Immunological Interest" and by Chothia and Lesk, J. Mol.

Biol. 196:901-917 (1987), which are incorporated herein by reference, where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues that encompass the CDRs as defined by each of the above cited references are set forth below in Table 1 as a comparison. The exact residue numbers that encompass a particular CDR will vary depending on the sequence and size of the CDR. Those skilled in the art can routinely determine which residues comprise a particular CDR given the variable region amino acid sequence of the antibody.

TABLE 1

CDR Definitions [1]

|  | Kabat | Chothia |
|---|---|---|
| VH CDR1 | 31-35 | 26-32 |
| VH CDR2 | 50-65 | 52-58 |
| VH CDR3 | 95-102 | 95-102 |
| VL CDR1 | 24-34 | 26-32 |
| VL CDR2 | 50-56 | 50-52 |
| VL CDR3 | 89-97 | 91-96 |

[1] Numbering of all CDR definitions in Table 1 is according to the numbering conventions set forth by Kabat et al. (see below).

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al. (1983) U.S. Dept. of Health and Human Services, "Sequence of Proteins of Immunological Interest." Unless otherwise specified, references to the numbering of specific amino acid residue positions in an anti-SEMA4D antibody or antigen-binding fragment, variant, or derivative thereof of the present disclosure are according to the Kabat numbering system.

Antibodies or antigen-binding fragments, variants, or derivatives thereof of the disclosure include, but are not limited to, polyclonal, monoclonal, multispecific and bispecific in which at least one arm is specific for SEMA4D, human, humanized, primatized, or chimeric antibodies, single-chain antibodies, epitope-binding fragments, e.g., Fab, Fab' and F(ab')$_2$, Fd, Fvs, single-chain Fvs (scFv), disulfide-linked Fvs (sdFv), fragments comprising either a VL or VH domain, fragments produced by a Fab expression library, and anti-idiotypic (anti-Id) antibodies (including, e.g., anti-Id antibodies to anti-SEMA4D antibodies disclosed herein). ScFv molecules are known in the art and are described, e.g., in U.S. Pat. No. 5,892,019. Immunoglobulin or antibody molecules of the disclosure can be of any type (e.g., IgG, IgE, IgM, IgD, IgA, and IgY), class (e.g., IgG1, IgG2, IgG3, IgG4, IgA1, and IgA2, etc.), or subclass of immunoglobulin molecule.

As used herein, the term "heavy chain portion" includes amino acid sequences derived from an immunoglobulin heavy chain. In certain embodiments, a polypeptide comprising a heavy chain portion comprises at least one of: a VH domain, a CH1 domain, a hinge (e.g., upper, middle, and/or lower hinge region) domain, a CH2 domain, a CH3 domain, or a variant or fragment thereof. For example, a binding polypeptide for use in the disclosure can comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, a polypeptide of the disclosure comprises a polypeptide chain comprising a CH3 domain. Further, a binding polypeptide for use in the disclosure can lack at least a portion of a CH2 domain (e.g., all or part of a CH2 domain). As set forth above, it will be understood by one of ordinary skill in the art that these domains (e.g., the heavy chain portions) can be modified such that they vary in amino acid sequence from the naturally occurring immunoglobulin molecule.

In certain anti-SEMA4D antibodies, or antigen-binding fragments, variants, or derivatives thereof disclosed herein, the heavy chain portions of one polypeptide chain of a multimer are identical to those on a second polypeptide chain of the multimer. Alternatively, heavy chain portion-containing monomers of the disclosure are not identical. For example, each monomer can comprise a different target binding site, forming, for example, a bispecific antibody.

The heavy chain portions of a binding molecule for use in the methods disclosed herein can be derived from different immunoglobulin molecules. For example, a heavy chain portion of a polypeptide can comprise a CH1 domain derived from an IgG1 molecule and a hinge region derived from an IgG3 molecule. In another example, a heavy chain portion can comprise a hinge region derived, in part, from an IgG1 molecule and, in part, from an IgG3 molecule. In another example, a heavy chain portion can comprise a chimeric hinge derived, in part, from an IgG1 molecule and, in part, from an IgG4 molecule.

As used herein, the term "light chain portion" includes amino acid sequences derived from an immunoglobulin light chain, e.g., a kappa or lambda light chain. In some aspects, the light chain portion comprises at least one of a VL or CL domain.

Anti-SEMA4D antibodies, or antigen-binding fragments, variants, or derivatives thereof disclosed herein can be described or specified in terms of the epitope(s) or portion(s) of an antigen, e.g., a target polypeptide disclosed herein (e.g., SEMA4D) that they recognize or specifically bind. The portion of a target polypeptide that specifically interacts with the antigen binding domain of an antibody is an "epitope," or an "antigenic determinant." A target polypeptide can comprise a single epitope, but typically comprises at least two epitopes, and can include any number of epitopes, depending on the size, conformation, and type of antigen. Furthermore, it should be noted that an "epitope" on a target polypeptide can be or can include non-polypeptide elements, e.g., an epitope can include a carbohydrate side chain.

The minimum size of a peptide or polypeptide epitope for an antibody is thought to be about four to five amino acids. Peptide or polypeptide epitopes can contain, e.g., at least seven, at least nine or between at least about 15 to about 30 amino acids. Since a CDR can recognize an antigenic peptide or polypeptide in its tertiary form, the amino acids comprising an epitope need not be contiguous, and in some cases, can be on separate peptide chains. A peptide or polypeptide epitope recognized by anti-SEMA4D antibodies of the present disclosure can contain a sequence of at least 4, at least 5, at least 6, at least 7, at least 8, at least 9, at least 10, at least 15, at least 20, at least 25, or between about 15 to about 30 contiguous or non-contiguous amino acids of SEMA4D.

By "specifically binds," it is generally meant that an antibody binds to an epitope via its antigen binding domain, and that the binding entails some complementarity between the antigen binding domain and the epitope. According to this definition, an antibody is said to "specifically bind" to an epitope when it binds to that epitope, via its antigen binding domain more readily than it would bind to a random, unrelated epitope. The term "specificity" is used herein to qualify the relative affinity by which a certain antibody binds to a certain epitope. For example, antibody "A" can be deemed to have a higher specificity for a given epitope than antibody "B," or antibody "A" can be said to bind to epitope "C" with a higher specificity than it has for related epitope "D."

By "preferentially binds," it is meant that the antibody specifically binds to an epitope more readily than it would bind to a related, similar, homologous, or analogous epitope. Thus, an antibody that "preferentially binds" to a given epitope would more likely bind to that epitope than to a related epitope, even though such an antibody can cross-react with the related epitope.

By way of non-limiting example, an antibody can be considered to bind a first epitope preferentially if it binds the first epitope with a dissociation constant ($K_D$) that is less than the antibody's $K_D$ for the second epitope. In another non-limiting example, an antibody can be considered to bind a first antigen preferentially if it binds the first epitope with an affinity that is at least one order of magnitude less than the antibody's $K_D$ for the second epitope. In another non-limiting example, an antibody can be considered to bind a first epitope preferentially if it binds the first epitope with an affinity that is at least two orders of magnitude less than the antibody's $K_D$ for the second epitope.

In another non-limiting example, an antibody can be considered to bind a first epitope preferentially if it binds the first epitope with an off rate (k(off)) that is less than the antibody's k(off) for the second epitope. In another non-limiting example, an antibody can be considered to bind a first epitope preferentially if it binds the first epitope with an affinity that is at least one order of magnitude less than the antibody's k(off) for the second epitope. In another non-limiting example, an antibody can be considered to bind a first epitope preferentially if it binds the first epitope with an affinity that is at least two orders of magnitude less than the antibody's k(off) for the second epitope. An antibody or antigen-binding fragment, variant, or derivative disclosed herein can be said to bind a target polypeptide disclosed herein (e.g., SEMA4D, e.g., human, murine, or both human and murine SEMA4D) or a fragment or variant thereof with an off rate (k(off)) of less than or equal to $5\times10^{-2}$ sec$^{-1}$, $10^{-2}$ sec$^{-1}$, $5\times10^{-3}$ sec$^{-1}$ or $10^{-3}$ sec$^{-1}$. In certain aspects, an antibody of the disclosure can be said to bind a target polypeptide disclosed herein (e.g., SEMA4D, e.g., human, murine, or both human and murine SEMA4D) or a fragment or variant thereof with an off rate (k(off)) less than or equal to $5\times10^{-4}$ sec$^{-1}$, $10^{-4}$ sec$^{-1}$, $5\times10^{-5}$ sec$^{-1}$, or $10^{-5}$ sec$^{-1}$, $5\times10^{-6}$ sec$^{-1}$, $10^{-6}$ sec$^{-1}$, $5\times10^{-7}$ sec$^{-1}$ or $10^{-7}$ sec$^{-1}$.

An antibody or antigen-binding fragment, variant, or derivative disclosed herein can be said to bind a target polypeptide disclosed herein (e.g., SEMA4D, e.g., human, murine, or both human and murine SEMA4D) or a fragment or variant thereof with an on rate (k(on)) of greater than or equal to $10^3$ M$^{-1}$ sec$^{-1}$, $5\times10^3$ M$^{-1}$ sec$^{-1}$, $10^4$ M$^{-1}$ sec$^{-1}$ or $5\times10^4$ M$^{-1}$ sec$^{-1}$. In some embodiments, an antibody of the disclosure cab be said to bind a target polypeptide disclosed herein (e.g., SEMA4D, e.g., human, murine, or both human and murine SEMA4D) or a fragment or variant thereof with an on rate (k(on)) greater than or equal to $10^5$ M$^{-1}$ sec$^{-1}$, $5\times10^5$ M$^{-1}$ sec$^{-1}$, $10^6$ M$^{-1}$ sec$^{-1}$, or $5\times10^6$ M$^{-1}$ sec$^{-1}$ or $10^7$ M$^{-1}$ sec$^{-1}$.

An antibody is said to competitively inhibit binding of a reference antibody to a given epitope if it preferentially binds to that epitope to the extent that it blocks, to some degree, binding of the reference antibody to the epitope. Competitive inhibition can be determined by any method known in the art, for example, competition ELISA assays. An antibody can be said to competitively inhibit binding of the reference antibody to a given epitope by at least 90%, at least 80%, at least 70%, at least 60%, or at least 50%.

As used herein, the term "affinity" refers to a measure of the strength of the binding of an individual epitope with the CDR of an immunoglobulin molecule. See, e.g., Harlow et al. (1988) Antibodies: A Laboratory Manual (Cold Spring Harbor Laboratory Press, 2nd ed.) pages 27-28. As used herein, the term "avidity" refers to the overall stability of the complex between a population of immunoglobulins and an antigen, that is, the functional combining strength of an immunoglobulin mixture with the antigen. See, e.g., Harlow at pages 29-34. Avidity is related to both the affinity of individual immunoglobulin molecules in the population with specific epitopes, and also the valences of the immunoglobulins and the antigen. For example, the interaction between a bivalent monoclonal antibody and an antigen with a highly repeating epitope structure, such as a polymer, would be one of high avidity.

Anti-SEMA4D antibodies or antigen-binding fragments, variants, or derivatives thereof of the disclosure can also be described or specified in terms of their cross-reactivity. As used herein, the term "cross-reactivity" refers to the ability of an antibody, specific for one antigen, to react with a second antigen; a measure of relatedness between two different antigenic substances. Thus, an antibody is cross reactive if it binds to an epitope other than the one that induced its formation. The cross reactive epitope generally contains many of the same complementary structural features as the inducing epitope, and in some cases, can actually fit better than the original.

For example, certain antibodies have some degree of cross-reactivity, in that they bind related, but non-identical epitopes, e.g., epitopes with at least 95%, at least 90%, at least 85%, at least 80%, at least 75%, at least 70%, at least 65%, at least 60%, at least 55%, and at least 50% identity (as calculated using methods known in the art and described herein) to a reference epitope. An antibody can be said to have little or no cross-reactivity if it does not bind epitopes with less than 95%, less than 90%, less than 85%, less than 80%, less than 75%, less than 70%, less than 65%, less than 60%, less than 55%, and less than 50% identity (as calculated using methods known in the art and described herein) to a reference epitope. An antibody can be deemed "highly specific" for a certain epitope, if it does not bind any other analogue, ortholog, or homolog of that epitope.

Anti-SEMA4D binding molecules, e.g., antibodies or antigen-binding fragments, variants or derivatives thereof, of the disclosure can also be described or specified in terms of their binding affinity to a polypeptide of the disclosure, e.g., SEMA4D, e.g., human, murine, or both human and murine SEMA4D. In certain aspects, the binding affinities include those with a dissociation constant or Kd less than $5\times10^{-2}$ M, $10^{-2}$ M, $5\times10^{-3}$M, $10^{-3}$ M, $5\times10^{-4}$M, $10^{-4}$M, $5\times10^{-5}$M, $10^{-5}$ M, $5\times10^{-6}$ M, $10^{-6}$ M, $5\times10^{-7}$M, $10^{-7}$ M, $5\times10^{-8}$M, $10^{-8}$M, $5\times10^{-9}$M, $10^{-9}$M, $5\times10^{-10}$ M, $10^{-10}$ M $5\times10^{-11}$M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M. In certain embodiments, the anti-SEMA4D binding molecule, e.g., an antibody or antigen binding fragment thereof, of the disclosure binds human SEMA4D with a Kd of about $5\times10^{-9}$ to about $6\times10^{-9}$. In another embodiment, the anti-SEMA4D binding molecule, e.g., an antibody or antigen binding fragment thereof, of the disclosure binds murine SEMA4D with a Kd of about $1\times10^{-9}$ to about $2\times10^{-9}$.

As used herein, the term "chimeric antibody" will be held to mean any antibody wherein the immunoreactive region or site is obtained or derived from a first species and the constant region (which can be intact, partial or modified in accordance with the instant disclosure) is obtained from a second species. In certain embodiments the target binding region or site will be from a non-human source (e.g., mouse or primate) and the constant region is human.

As used herein, the term "engineered antibody" refers to an antibody in which the variable domain in either the heavy or light chain or both is altered by at least partial replacement of one or more CDRs from an antibody of known specificity and, if necessary, by partial framework region replacement and sequence changing. Although the CDRs can be derived from an antibody of the same class or even subclass as the antibody from which the framework regions are derived, it is envisaged that the CDRs will be derived from an antibody of different class, or from an antibody from a different species. An engineered antibody in which one or more "donor" CDRs from a non-human antibody of known specificity is grafted into a human heavy or light chain framework region is referred to herein as a "humanized antibody." It is not always necessary to replace all of the CDRs with the complete CDRs from the donor variable domain to transfer the antigen binding capacity of one variable domain to another. Rather, one can transfer just those residues needed to maintain the activity of the target binding site need be transferred.

It is further recognized that the framework regions within the variable domain in a heavy or light chain, or both, of a humanized antibody can comprise solely residues of human origin, in which case these framework regions of the humanized antibody are referred to as "fully human framework regions" (for example, MAbs VX15/2503 or 67, disclosed in U.S. Patent Appl. Publication No. US 2010/0285036 A1 as MAb 2503, incorporated herein by reference in its entirety). Alternatively, one or more residues of the framework region(s) of the donor variable domain can be engineered within the corresponding position of the human framework region(s) of a variable domain in a heavy or light chain, or both, of a humanized antibody if necessary to maintain proper binding or to enhance binding to the SEMA4D antigen. A human framework region that has been engineered in this manner would thus comprise a mixture of human and donor framework residues and is referred to herein as a "partially human framework region."

For example, humanization of an anti-SEMA4D antibody can be essentially performed following the method of Winter and co-workers (Jones et al., Nature 321:522-525 (1986); Riechmann et al., Nature 332:323-327 (1988); Verhoeyen et al., Science 239:1534-1536 (1988)), by substituting rodent or mutant rodent CDRs or CDR sequences for the corresponding sequences of a human anti-SEMA4D antibody. See also U.S. Pat. Nos. 5,225,539; 5,585,089; 5,693,761; 5,693,762; 5,859,205; herein incorporated by reference. The resulting humanized anti-SEMA4D antibody would comprise at least one rodent or mutant rodent CDR within the fully human framework regions of the variable domain of the heavy and/or light chain of the humanized antibody. In some instances, residues within the framework regions of one or more variable domains of the humanized anti-SEMA4D antibody are replaced by corresponding non-human (for example, rodent) residues (see, for example, U.S. Pat. Nos. 5,585,089; 5,693,761; 5,693,762; and 6,180, 370), in which case the resulting humanized anti-SEMA4D antibody would comprise partially human framework regions within the variable domain of the heavy and/or light chain.

Furthermore, humanized antibodies can comprise residues that are not found in the recipient antibody or in the donor antibody. These modifications are made to further refine antibody performance (e.g., to obtain desired affinity). In general, the humanized antibody will comprise substantially all of at least one, and typically two, variable domains, in which all or substantially all of the CDRs correspond to those of a non-human immunoglobulin and all or substantially all of the framework regions are those of a human immunoglobulin sequence. The humanized antibody optionally also will comprise at least a portion of an immunoglobulin constant region (Fc), typically that of a human immunoglobulin. For further details see Jones et al., Nature 331:522-525 (1986); Riechmann et al., Nature 332:323-329 (1988); and Presta, Curr. Op. Struct. Biol. 2:593-596 (1992); herein incorporated by reference. Accordingly, such "humanized" antibodies can include antibodies wherein substantially less than an intact human variable domain has been substituted by the corresponding sequence from a non-human species. In practice, humanized antibodies are typically human antibodies in which some CDR residues and possibly some framework residues are substituted by residues from analogous sites in rodent antibodies. See, for example, U.S. Pat. Nos. 5,225,539; 5,585,089; 5,693,761; 5,693,762; 5,859,205. See also U.S. Pat. No. 6,180,370, and International Publication No. WO 01/27160, where humanized antibodies and techniques for producing humanized antibodies having improved affinity for a predetermined antigen are disclosed.

As used herein, the term "healthcare provider" refers to individuals or institutions that directly interact and administer to living subjects, e.g., human patients. Non-limiting examples of healthcare providers include doctors, nurses, technicians, therapist, pharmacists, counselors, alternative medicine practitioners, medical facilities, doctor's offices, hospitals, emergency rooms, clinics, urgent care centers, alternative medicine clinics/facilities, and any other entity providing general and/or specialized treatment, assessment, maintenance, therapy, medication, and/or advice relating to all, or any portion of, a patient's state of health, including but not limited to general medical, specialized medical, surgical, and/or any other type of treatment, assessment, maintenance, therapy, medication and/or advice.

As used herein, the term "healthcare benefits provider" encompasses individual parties, organizations, or groups providing, presenting, offering, paying for in whole or in part, or being otherwise associated with giving a patient access to one or more healthcare benefits, benefit plans, health insurance, and/or healthcare expense account programs.

As used herein, the term "clinical laboratory" refers to a facility for the examination or processing of materials or images derived from a living subject, e.g., a human being. Non-limiting examples of processing include biological, biochemical, serological, chemical, immunohematological, hematological, biophysical, cytological, pathological, genetic, image based, or other examination of materials derived from the human body or of any or all of the human body for the purpose of providing information, e.g., for the diagnosis, prevention, or treatment of any disease or impairment of, or the assessment of the health of living subjects, e.g., human beings. These examinations can also include procedures to collect or otherwise obtain an image, a sample, prepare, determine, measure, or otherwise describe the presence or absence of various substances in the body of a living subject, e.g., a human being, or a sample obtained from the body of a living subject, e.g., a human being.

II. Target Polypeptide Description

As used herein, the terms "Semaphorin 4D," "SEMA4D" and "SEMA4D polypeptide" are used interchangeably, as are "SEMA4D" and "Sema4D." SEMA4D is a transmembrane signaling protein implicated in several processes that may increase neuroinflammation, including glial cell activation, inhibition of oligodendrocyte and astrocyte migration, inhibition of neurodevelopment, and inducement of apoptosis. In certain embodiments, SEMA4D is expressed on the surface of or secreted by a cell. In another embodiment, SEMA4D is membrane bound. In another embodiments, SEMA4D is soluble, e.g., sSEMA4D. In other embodiments, SEMA4D can include a full-sized SEMA4D or a fragment thereof, or a SEMA4D variant polypeptide, wherein the fragment of SEMA4D or SEMA4D variant polypeptide retains some or all functional properties of the full-sized SEMA4D.

The full-sized human SEMA4D protein is a homodimeric transmembrane protein consisting of two polypeptide chains of 150 kDa. SEMA4D belongs to the semaphorin family of cell surface receptors and is also referred to as CD100. Both human and mouse SEMA4D/Sema4D are proteolytically cleaved from their transmembrane form to generate 120-kDa soluble forms, indicating the existence of two Sema4D isoforms (Kumanogoh et al., J. Cell Science 116(7):3464 (2003)). Semaphorins consist of soluble and membrane-bound proteins that were originally defined as axonal-guidance factors during development which play an important role in establishing precise connections between neurons and their appropriate target. Structurally considered a class IV semaphorin, SEMA4D consists of an amino-terminal signal sequence followed by a characteristic 'Sema' domain, which contains 17 conserved cysteine residues, an Ig-like domain, a lysine-rich stretch, a hydrophobic transmembrane region, and a cytoplasmic tail.

A polypeptide chain of SEMA4D can include a signal sequence of about 13 amino acids and further includes a semaphorin domain of about 512 amino acids, an immunoglobulin-like (Ig-like) domain of about 65 amino acids, a lysine-rich stretch of 104 amino acids, a hydrophobic transmembrane region of about 19 amino acids, and a cytoplasmic tail of 110 amino acids. A consensus site for tyrosine phosphorylation in the cytoplasmic tail supports the predicted association of SEMA4D with a tyrosine kinase (Schlossman, et al., Eds. (1995) Leucocyte Typing V (Oxford University Press, Oxford).

SEMA4D is known to have at least three functional receptors, Plexin-B1, Plexin-B2 and CD72. Plexin-B1, is expressed in non-lymphoid tissues and has been shown to be a high affinity (1 nM) receptor for SEMA4D (Tamagnone et al., Cell 99:71-80 (1999)). SEMA4D stimulation of Plexin-B1 signaling has been shown to induce growth cone collapse of neurons, and to induce process extension collapse and apoptosis of oligodendrocytes (Giraudon et al., J. Immunol. 172:1246-1255 (2004); Giraudon et al., NeuroMolecular Med. 7:207-216 (2005)). After binding to SEMA4D, Plexin-B1 signaling mediates the inactivation of R-Ras, leading to a decrease in the integrin mediated attachment to the extracellular matrix, as well as to activation of RhoA, leading to reorganization of the cytoskeleton and cell migration. See Kruger et al., Nature Rev. Mol. Cell Biol. 6:789-800 (2005); Pasterkamp, TRENDS in Cell Biology 15:61-64 (2005)). Plexin-B2, on the other hand, has an intermediate affinity for SEMA4D and recent reports indicate that Plexin-B2 regulates migration of cortical neurons and proliferation and migration of neuroblasts in the adult subventricular zone (Azzarelli et al, Nat Commun 2014 Feb. 27, 5:3405, DOI: 10.1038/ncomms4405; and Saha et al., J. Neuroscience, 2012 Nov. 21, 32(47):16892-16905).

In lymphoid tissues CD72 is utilized as a low affinity (300 nM) SEMA4D receptor (Kumanogoh et al., Immunity 13:621-631 (2000)). B cells and APCs express CD72, and anti-CD72 antibodies have many of the same effects as sSEMA4D, such as enhancement of CD40-induced B cell responses and B cell shedding of CD23. CD72 is thought to act as a negative regulator of B cell responses by recruiting the tyrosine phosphatase SHP-1, which can associate with many inhibitory receptors. Interaction of SEMA4D with CD72 results in the dissociation of SHP-1, and the loss of this negative activation signal. SEMA4D has been reported to promote T cell stimulation and B cell aggregation and survival in vitro. The addition of SEMA4D-expressing cells or sSEMA4D enhances CD40-induced B cell proliferation and immunoglobulin production in vitro, and accelerates in vivo antibody responses (Ishida et al., Inter. Immunol. 15:1027-1034 (2003); Kumanogoh and H. Kukutani, Trends in Immunol. 22:670-676 (2001)). sSEMA4D enhances the CD40 induced maturation of dendritic cells (DCs), including up-regulation of costimulatory molecules and increased secretion of IL-12. In addition, sSEMA4D can inhibit immune cell migration, which can be reversed by addition of blocking anti-SEMA4D antibodies (Elhabazi et al., J. Immunol. 166:4341-4347 (2001); Delaire et al., J. Immunol. 166:4348-4354 (2001)).

Sema4D is expressed at high levels in lymphoid organs, including the spleen, thymus, and lymph nodes, and in non-lymphoid organs, such as the brain, heart, and kidney. In lymphoid organs, Sema4D is abundantly expressed on resting T cells but only weakly expressed on resting B cells and antigen-presenting cells (APCs), such as DCs. Cellular activation increases the surface expression of SEMA4D as well as the generation of soluble SEMA4D (sSEMA4D).

The expression pattern of SEMA4D suggests that it plays an important physiological as well as pathological role in the immune system. SEMA4D has been shown to promote B cell activation, aggregation and survival; enhance CD40-induced proliferation and antibody production; enhance antibody response to T cell dependent antigens; increase T cell proliferation; enhance dendritic cell maturation and ability to stimulate T cells; and is directly implicated in demyelination and axonal degeneration (Shi et al., Immunity 13:633-642 (2000); Kumanogoh et al., J Immunol 169:1175-1181 (2002); and Watanabe et al., J Immunol 167:4321-4328 (2001)).

SEMA4D knock out (SEMA4D−/−) mice have provided additional evidence that SEMA4D plays an important role in both humoral and cellular immune responses. There are no known major abnormalities of non-lymphoid tissues in SEMA4D−/− mice. DCs from the SEMA4D−/− mice have poor allostimulatory ability and show defects in expression of costimulatory molecules, which can be rescued by the addition of sSEMA4D. Mice deficient in SEMA4D (SEMA4D−/−) fail to develop experimental autoimmune encephalomyelitis induced by myelin oligodendrocyte glycoprotein peptide, because myelin oligodendrocyte glycoprotein-specific T cells are poorly generated in the absence of SEMA4D (Kumanogoh et al., J Immunol 169:1175-1181 (2002)). A significant amount of soluble SEMA4D is also detected in the sera of autoimmunity-prone MRL/lpr mice (model of systemic autoimmune diseases such as SLE), but not in normal mice. Further, the levels of sSEMA4D correlate with levels of auto-antibodies and increase with age (Wang et al., Blood 97:3498-3504 (2001)). Soluble SEMA4D has also been shown to accumulate in the cerebral spinal fluid and sera of patients with demyelinating disease, and sSEMA4D induces apoptosis of human pluripotent neural precursors (Dev cells), and both inhibit process extension and induce apoptosis of rat oligodendrocytes in vitro (Giraudon et al., J Immunol 172(2):1246-1255 (2004)). This apoptosis was blocked by an anti-SEMA4D MAb.

The inventors have previously shown that neurons in the brains of both experimental animals and patients undergoing stress or injury in the course of progressive neurodegenerative disease, including Huntington's and Alzheimer's disease and animal models of these diseases, upregulate SEMA4D. (U.S. Pat. Nos. 9,598,495 and 10,385,136) Astrocytes, located in close proximity to neurons, express high affinity plexin-B1 receptors for SEMA4D and are triggered by binding to SEMA4D ligand to undergo changes in morphology and gene expression associated with inflammatory transformation. Blocking this inflammatory signalling pathway with Antibody to SEMA4D has been shown to ameliorate pathology in animal models of HD (Southwell, A. L., et al. Anti-semaphorin 4D immunotherapy ameliorates neuropathology and some cognitive impairment in the YAC128 mouse model of Huntington disease. *Neurobiol. Dis* 76, 46-56 (2015)), AD and multiple sclerosis (Smith, E. S., et al. SEMA4D compromises blood-brain barrier, activates microglia, and inhibits remyelination in neurodegenerative disease. *Neurobiol. Dis* 73, 254-268 (2014) and, most recently, to prevent loss of brain metabolic activity in patients who express the gene mutation that gives rise to Huntington's disease. The observation that SEMA4D is also upregulated in brain of female Mecp mice and evidence of a role for astrocytes (Lioy et al., Nature, 475(7357):497-500 (2012)) suggests that this same pathogenic pathway may be active and contribute to pathology in Rett syndrome.

III. Anti-SEMA4D Antibodies

Antibodies that bind SEMA4D have been described in the art. See, for example, U.S. Pat. No. 8,496,938, US Publ. Nos. 2008/0219971 A1, US 2010/0285036 A1, and US 2006/0233793 A1, International Patent Applications WO 93/14125, WO 2008/100995, and WO 2010/129917, and Herold et al., Int. Immunol. 7(1): 1-8 (1995), each of which is herein incorporated in its entirety by reference.

The disclosure generally relates to a method of alleviating symptoms in a subject having Rett syndrome, e.g., a human patient, comprising administration of an antibody which specifically binds to SEMA4D, or an antigen-binding fragment, variant, or derivative thereof. In certain embodiments, the antibody blocks the interaction of SEMA4D with one or more of its receptors, e.g., Plexin-B1. Anti-SEMA4D antibodies having these properties can be used in the methods provided herein. Antibodies that can be used include, but are not limited to MAbs VX15/2503, 67, and 76 and antigen-binding fragments, variants, or derivatives thereof which are fully described in US 2010/0285036 A1. Additional antibodies which can be used in the methods provided herein include the BD16 and BB18 antibodies described in US 2006/0233793 A1 as well as antigen-binding fragments, variants, or derivatives thereof; or any of MAb 301, MAb 1893, MAb 657, MAb 1807, MAb 1656, MAb 1808, Mab 59, MAb 2191, MAb 2274, MAb 2275, MAb 2276, MAb 2277, MAb 2278, MAb 2279, MAb 2280, MAb 2281, MAb 2282, MAb 2283, MAb 2284, and MAb 2285, as well as any fragments, variants or derivatives thereof as described in US 2008/0219971 A1. In certain embodiments an anti-SEMA4D antibody for use in the methods provided herein binds human, murine, or both human and murine SEMA4D. Also useful are antibodies which bind to the same epitope as any of the aforementioned antibodies and/or antibodies which competitively inhibit any of the aforementioned antibodies.

In certain embodiments, an anti-SEMA4D antibody or antigen-binding fragment, variant, or derivative thereof useful in the methods provided herein has an amino acid sequence that has at least about 80%, about 85%, about 88%, about 89%, about 90%, about 91%, about 92%, about 93%, about 94%, or about 95% sequence identity to the amino acid sequence for a reference anti-SEMA4D antibody molecule, for example those described above. In a further embodiment, the binding molecule shares at least about 96%, about 97%, about 98%, about 99%, or 100% sequence identity to a reference antibody.

In another embodiment, an anti-SEMA4D antibody or antigen-binding fragment, variant, or derivative thereof useful in the methods provided herein comprises, consists essentially of, or consists of an immunoglobulin heavy chain variable domain (VH domain), where at least one of the CDRs of the VH domain has an amino acid sequence that is at least about 80%, about 85%, about 90%, about 95%, about 96%, about 97%, about 98%, about 99%, or identical to CDR1, CDR2 or CDR3 of SEQ ID NO: 6, 7, or 21.

In another embodiment, an anti-SEMA4D antibody or antigen-binding fragment, variant, or derivative thereof useful in the methods provided herein comprises, consists essentially of, or consists of an immunoglobulin heavy chain variable domain (VH domain), where at least one of the CDRs of the VH domain has an amino acid sequence that is at least about 80%, about 85%, about 90%, about 95%, about 96%, about 97%, about 98%, about 99%, or identical to SEQ ID NO: 3, SEQ ID NO: 4, or SEQ ID NO: 5.

In another embodiment, an anti-SEMA4D antibody or antigen-binding fragment, variant, or derivative thereof useful in the methods provided herein comprises, consists essentially of, or consists of an immunoglobulin heavy chain variable domain (VH domain), where at least one of the CDRs of the VH domain has an amino acid sequence that is at least about 80%, about 85%, about 90%, about 95%, about 96%, about 97%, about 98%, about 99%, or identical to SEQ ID NO: 22, SEQ ID NO: 23, or SEQ ID NO: 24.

In another embodiment, an anti-SEMA4D antibody or antigen-binding fragment, variant, or derivative thereof useful in the methods provided herein comprises, consists essentially of, or consists of an immunoglobulin heavy chain variable domain (VH domain), where at least one of the CDRs of the VH domain has an amino acid sequence identical, except for 1, 2, 3, 4, or 5 conservative amino acid substitutions, to SEQ ID NO: 3, SEQ ID NO: 4, or SEQ ID NO: 5.

In another embodiment, an anti-SEMA4D antibody or antigen-binding fragment, variant, or derivative thereof useful in the methods provided herein comprises, consists essentially of, or consists of an immunoglobulin heavy chain variable domain (VH domain), where at least one of the CDRs of the VH domain has an amino acid sequence identical, except for 1, 2, 3, 4, or 5 conservative amino acid substitutions, to SEQ ID NO: 22, SEQ ID NO: 23, or SEQ ID NO: 24.

In another embodiment, an anti-SEMA4D antibody or antigen-binding fragment, variant, or derivative thereof useful in the methods provided herein comprises, consists essentially of, or consists of a VH domain that has an amino acid sequence that is at least about 80%, about 85%, about 90%, about 91%, about 92%, about 93%, about 94%, about 95%, about 96%, about 97%, about 98%, about 99%, or 100% identical to SEQ ID NO: 6, SEQ ID NO: 7, or SEQ ID NO: 21, wherein an anti-SEMA4D antibody comprising the encoded VH domain specifically or preferentially binds to SEMA4D.

In another embodiment, an anti-SEMA4D antibody or antigen-binding fragment, variant, or derivative thereof useful in the methods provided herein comprises, consists essentially of, or consists of an immunoglobulin light chain variable domain (VL domain), where at least one of the CDRs of the VL domain has an amino acid sequence that is at least about 80%, about 85%, about 90%, about 95%, about 96%, about 97%, about 98%, about 99%, or identical to CDR1, CDR2 or CDR3 of SEQ ID NO: 11, 12, or SEQ ID NO: 25.

In another embodiment, an anti-SEMA4D antibody or antigen-binding fragment, variant, or derivative thereof useful in the methods provided herein comprises, consists essentially of, or consists of an immunoglobulin light chain variable domain (VL domain), where at least one of the CDRs of the VL domain has an amino acid sequence that is at least about 80%, about 85%, about 90%, about 95%, about 96%, about 97%, about 98%, about 99%, or identical to SEQ ID NO: 8, SEQ ID NO: 9, or SEQ ID NO: 10.

In another embodiment, an anti-SEMA4D antibody or antigen-binding fragment, variant, or derivative thereof useful in the methods provided herein comprises, consists essentially of, or consists of an immunoglobulin light chain variable domain (VL domain), where at least one of the CDRs of the VL domain has an amino acid sequence that is at least about 80%, about 85%, about 90%, about 95%, about 96%, about 97%, about 98%, about 99%, or identical to SEQ ID NO: 26, SEQ ID NO: 27, or SEQ ID NO: 28.

In another embodiment, an anti-SEMA4D antibody or antigen-binding fragment, variant, or derivative thereof useful in the methods provided herein comprises, consists essentially of, or consists of an immunoglobulin light chain variable domain (VL domain), where at least one of the CDRs of the VL domain has an amino acid sequence identical, except for 1, 2, 3, 4, or 5 conservative amino acid substitutions, to SEQ ID NO: 8, SEQ ID NO: 9, or SEQ ID NO: 10.

In another embodiment, an anti-SEMA4D antibody or antigen-binding fragment, variant, or derivative thereof useful in the methods provided herein comprises, consists essentially of, or consists of an immunoglobulin light chain variable domain (VL domain), where at least one of the CDRs of the VL domain has an amino acid sequence identical, except for 1, 2, 3, 4, or 5 conservative amino acid substitutions, to SEQ ID NO: 26, SEQ ID NO: 27, or SEQ ID NO: 28.

In a further embodiment, an anti-SEMA4D antibody or antigen-binding fragment, variant, or derivative thereof useful in the methods provided herein comprises, consists essentially of, or consists of a VL domain that has an amino acid sequence that is at least about 80%, about 85%, about 90%, about 91%, about 92%, about 93%, about 94%, about 95%, about 96%, about 97%, about 98%, about 99%, or 100% identical to SEQ ID NO: 11, SEQ ID NO: 12, or SEQ ID NO: 25, wherein an anti-SEMA4D antibody comprising the encoded VL domain specifically or preferentially binds to SEMA4D.

Also included for use in the methods provided herein are polypeptides encoding anti-SEMA4D antibodies, or antigen-binding fragments, variants, or derivatives thereof as described herein, polynucleotides encoding such polypeptides, vectors comprising such polynucleotides, and host cells comprising such vectors or polynucleotides, all for producing anti-SEMA4D antibodies, or antigen-binding fragments, variants, or derivatives thereof for use in the methods described herein.

Suitable biologically active variants of the anti-SEMA4D antibodies of the disclosure can be used in the methods of the present disclosure. Such variants will retain the desired binding properties of the parent anti-SEMA4D antibody. Methods for making antibody variants are generally available in the art.

Methods for mutagenesis and nucleotide sequence alterations are well known in the art. See, for example, Walker and Gaastra, eds. (1983) Techniques in Molecular Biology (MacMillan Publishing Company, New York); Kunkel, Proc. Natl. Acad. Sci. USA 82:488-492 (1985); Kunkel et al., Methods Enzymol. 154:367-382 (1987); Sambrook et al. (1989) Molecular Cloning: A Laboratory Manual (Cold Spring Harbor, N.Y.); U.S. Pat. No. 4,873,192; and the references cited therein; herein incorporated by reference. Guidance as to appropriate amino acid substitutions that do not affect biological activity of the polypeptide of interest can be found in the model of Dayhoff et al. (1978) in Atlas of Protein Sequence and Structure (Natl. Biomed. Res. Found., Washington, D.C.), pp. 345-352, herein incorporated by reference in its entirety. The model of Dayhoff et al. uses the Point Accepted Mutation (PAM) amino acid similarity matrix (PAM 250 matrix) to determine suitable conservative amino acid substitutions. In certain embodiments, conservative substitutions, such as exchanging one amino acid with another having similar properties can be used. Examples of conservative amino acid substitutions as taught by the PAM 250 matrix of the Dayhoff et al. model include, but are not limited to, Gly↔Ala, Val↔Ile↔Leu, Asp↔Glu, Lys↔Arg, Asn↔Gln, and Phe↔Trp↔Tyr.

In constructing variants of the anti-SEMA4D binding molecule, e.g., an antibody or antigen-binding fragment thereof, polypeptides of interest, modifications are made such that variants continue to possess the desired properties, e.g., being capable of specifically binding to a SEMA4D, e.g., human, murine, or both human and murine SEMA4D, e.g., expressed on the surface of or secreted by a cell and having SEMA4D blocking activity, as described herein. Obviously, any mutations made in the DNA encoding the variant polypeptide must not place the sequence out of reading frame and in certain embodiments will not create complementary regions that could produce secondary mRNA structure. See EP Patent Application Publication No. 75,444.

Methods for measuring anti-SEMA4D binding molecule, e.g., an antibody or antigen-binding fragment, variant, or derivative thereof, binding specificity include, but are not limited to, standard competitive binding assays, assays for monitoring immunoglobulin secretion by T cells or B cells, T cell proliferation assays, apoptosis assays, ELISA assays, and the like. See, for example, such assays disclosed in WO 93/14125; Shi et al., Immunity 13:633-642 (2000); Kumanogoh et al., J Immunol 169:1175-1181 (2002); Watanabe et al., J Immunol 167:4321-4328 (2001); Wang et al., Blood 97:3498-3504 (2001); and Giraudon et al., J Immunol 172(2):1246-1255 (2004), all of which are herein incorporated by reference.

When discussed herein whether any particular polypeptide, including the constant regions, CDRs, VH domains, or VL domains disclosed herein, is at least about 65%, about 70%, about 75%, about 80%, about 85%, about 90%, about 91%, about 92%, about 93%, about 94%, about 95%, about 96%, about 97%, about 98%, about 99%, or even about 100% identical to another polypeptide, the % identity can be determined using methods and computer programs/software known in the art such as, but not limited to, the BESTFIT program (Wisconsin Sequence Analysis Package, Version 8 for Unix, Genetics Computer Group, University Research Park, 575 Science Drive, Madison, Wis. 53711). BESTFIT uses the local homology algorithm of Smith and Waterman (1981) Adv. Appl. Math. 2:482-489, to find the best segment of homology between two sequences. When using BESTFIT or any other sequence alignment program to determine whether a particular sequence is, for example, 95% identical to a reference sequence according to the present disclosure, the parameters are set, of course, such that the percentage of identity is calculated over the full length of the reference polypeptide sequence and that gaps in homology of up to 5% of the total number of amino acids in the reference sequence are allowed.

For purposes of the present disclosure, percent sequence identity can be determined using the Smith-Waterman homology search algorithm using an affine gap search with a gap open penalty of 12 and a gap extension penalty of 2, BLOSUM matrix of 62. The Smith-Waterman homology search algorithm is taught in Smith and Waterman (1981) Adv. Appl. Math. 2:482-489. A variant can, for example, differ from a reference anti-SEMA4D antibody (e.g., MAb VX15/2503, 67, or 76) by as few as 1 to 15 amino acid residues, as few as 1 to 10 amino acid residues, such as 6-10, as few as 5, as few as 4, 3, 2, or even 1 amino acid residue.

Percentage of "sequence identity" can also be determined by comparing two optimally aligned sequences over a comparison window. In order to optimally align sequences for comparison, the portion of a polynucleotide or polypeptide sequence in the comparison window can comprise additions or deletions termed gaps while the reference sequence is kept constant. An optimal alignment is that alignment which, even with gaps, produces the greatest possible number of "identical" positions between the reference and comparator sequences. Percentage "sequence identity" between two sequences can be determined using the version of the program "BLAST 2 Sequences" which was available from the National Center for Biotechnology Information as of Sep. 1, 2004, which program incorporates the programs BLASTN (for nucleotide sequence comparison) and BLASTP (for polypeptide sequence comparison), which programs are based on the algorithm of Karlin and Altschul (Proc. Natl. Acad. Sci. USA 90(12):5873-5877, 1993). When utilizing "BLAST 2 Sequences," parameters that were default parameters as of Sep. 1, 2004, can be used for word size (3), open gap penalty (11), extension gap penalty (1), gap drop-off (50), expect value (10) and any other required parameter including but not limited to matrix option.

The constant region of an anti-SEMA4D antibody can be mutated to alter effector functio\n in a number of ways. For example, see U.S. Pat. No. 6,737,056B1 and U.S. Patent Application Publication No. 2004/0132101A1, which disclose Fc mutations that optimize antibody binding to Fc receptors.

In certain anti-SEMA4D antibodies or fragments, variants or derivatives thereof useful in the methods provided herein, the Fc portion can be mutated to decrease effector function using techniques known in the art. For example, the deletion or inactivation (through point mutations or other means) of a constant region domain can reduce Fc receptor binding of the circulating modified antibody thereby increasing tumor localization. In other cases, constant region modifications consistent with the instant disclosure moderate complement binding and thus reduce the serum half-life. Yet other modifications of the constant region can be used to modify disulfide linkages or oligosaccharide moieties that allow for enhanced localization due to increased antigen specificity or antibody flexibility. The resulting physiological profile, bioavailability and other biochemical effects of the modifications, such as tumor localization, biodistribution and serum half-life, can easily be measured and quantified using well known immunological techniques without undue experimentation. Anti-SEMA4D antibodies for use in the methods provided herein include derivatives that are modified, e.g., by the covalent attachment of any type of molecule to the antibody such that covalent attachment does not prevent the antibody from specifically binding to its cognate epitope. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications can be carried out by known techniques, including, but not limited to specific chemical cleavage, acetylation, formylation, etc. Additionally, the derivative can contain one or more non-classical amino acids.

A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity (e.g., the ability to bind an anti-SEMA4D polypeptide, to block SEMA4D interaction with its receptor, or to alleviate symptoms associated with a neurodegenerative disorder in a patient).

For example, it is possible to introduce mutations only in framework regions or only in CDR regions of an antibody molecule. Introduced mutations can be silent or neutral missense mutations, i.e., have no, or little, effect on an antibody's ability to bind antigen. These types of mutations can be useful to optimize codon usage, or improve a hybridoma's antibody production. Alternatively, non-neutral missense mutations can alter an antibody's ability to bind antigen. One of skill in the art would be able to design and test mutant molecules with desired properties such as no alteration in antigen binding activity or alteration in binding activity (e.g., improvements in antigen binding activity or change in antibody specificity). Following mutagenesis, the encoded protein can routinely be expressed and the functional and/or biological activity of the encoded protein, (e.g., ability to immunospecifically bind at least one epitope of a SEMA4D polypeptide) can be determined using techniques described herein or by routinely modifying techniques known in the art.

In certain embodiments, the anti-SEMA4D antibodies for use in the methods provided herein comprise at least one optimized complementarity-determining region (CDR). By "optimized CDR" is intended that the CDR has been modified and optimized to improve binding affinity and/or anti-SEMA4D activity that is imparted to an anti-SEMA4D antibody comprising the optimized CDR. "Anti-SEMA4D activity" or "SEMA4D blocking activity" can include activity which modulates one or more of the following activities associated with SEMA4D: B cell activation, aggregation and survival; CD40-induced proliferation and antibody production; antibody response to T cell dependent antigens; T cell or other immune cell proliferation; dendritic cell maturation; demyelination and axonal degeneration; apoptosis of pluripotent neural precursors and/or oligodendrocytes; induction of endothelial cell migration; inhibition of spontaneous monocyte migration; regulation of glial cell (astrocyte, microglia, oligodendrocyte, precursors) function and inflammatory activity; binding to cell surface Plexin-B1 or other receptor, or any other activity associated with soluble SEMA4D or SEMA4D that is expressed on the surface of SEMA4D+ cells. Anti-SEMA4D activity can also be attributed to a decrease in incidence or severity of diseases associated with SEMA4D expression, including, but not limited to, certain types of cancers including lymphomas, autoimmune diseases, inflammatory diseases including central nervous system (CNS) and peripheral nervous system (PNS) inflammatory diseases, transplant rejections, and invasive angiogenesis. Examples of optimized antibodies based on murine anti-SEMA4D MAbs BD16 and BB18, were described in US Publ. No. 2008/0219971 A1, International Patent Application WO 93/14125 and Herold et al., Int. Immunol. 7(1): 1-8 (1995), each of which are herein incorporated by reference in their entirety. The modifications can involve replacement of amino acid residues within the CDR such that an anti-SEMA4D antibody retains specificity for the SEMA4D antigen and has improved binding affinity and/or improved anti-SEMA4D activity.

IV. MeCP2

The MECP2 (methyl CpG binding protein 2) gene encodes the protein MeCP2. (Lewis et al. (June 1992). Cell. 69 (6): 905-14). MeCP2 protein is found in all cells in the body, including the brain, where it acts as a transcriptional repressor and activator, depending on the context. In the brain, it is found in high concentrations in neurons and to a lower extent in astrocytes and is associated with maturation of the central nervous system (CNS) and in forming synaptic contacts. (Luikenhuis et al., (April 2004) *Proc. Natl. Acad. Sci. U.S.A.* 101 (16): 6033-8). MeCP2 appears to be essential for the normal function of nerve cells and is particularly important for mature nerve cells, where it is present in high levels. On the whole, it has been found that MeCP2 affects glutamate clearance, cytokine production, electrical signaling, and neuronal morphology, all of which play a role in neurodevelopment.

Many mutations have been associated with loss of expression of the MECP2 gene and have been identified in Rett syndrome patients. MECP2 gene mutations are the cause of most cases of Rett syndrome. These mutations include changes in single DNA base pairs (SNP), insertions or deletions of DNA in the MECP2 gene, and changes that affect RNA splicing. Mutations in the MeCP2 gene alter the structure of the MeCP2 protein or lead to reduced amounts of the protein. As a result, the protein is unable to bind to DNA (MeCP2 protein epigenetically modulates gene expression through genome-wide binding to methylated CpG dinucleotides) or turn other genes on or off. Genes that are normally repressed by MeCP2 remain active when their products are not needed. Other genes that are normally activated by MeCP2 remain inactive leading to a lack of gene product. This defect probably disrupts the normal functioning of nerve cells, leading to the symptoms of Rett syndrome.

V. Characteristic Symptoms of Rett Syndrome

Scientists generally describe four stages of Rett syndrome. Stage I, called early onset, typically begins between 6 and 18 months of age. This stage is often overlooked because symptoms of the disorder may be somewhat vague and the subtle slowing of development may not be noticed at first. The infant may begin to show less eye contact and have reduced interest in toys. There may be delays in gross motor skills such as sitting or crawling. Hand-wringing and decreasing head growth may occur, but not enough to draw attention. This stage usually lasts for a few months but can continue for more than a year.

Stage II, or the rapid destructive stage, usually begins between ages 1 and 4 and may last for weeks or months. Its onset may be rapid or gradual as the child loses purposeful hand skills and spoken language. Characteristic hand movements such as wringing, washing, clapping, or tapping, as well as repeatedly moving the hands to the mouth often begin during this stage. The child may hold the hands clasped behind the back or held at the sides, with random touching, grasping, and releasing. The movements continue while the child is awake but disappear during sleep. Breathing irregularities such as episodes of apnea and hyperventilation may occur, although breathing usually improves during sleep. Some girls also display autistic-like symptoms such as loss of social interaction and communication. Walking may be unsteady and initiating motor movements can be difficult. Slowed head growth is usually noticed during this stage.

Stage III, or the plateau or pseudo-stationary stage, usually begins between ages 2 and 10 and can last for years. Apraxia, motor problems, and seizures are prominent during this stage. However, there may be improvement in behavior, with less irritability, crying, and autistic-like features. A girl in stage III may show more interest in her surroundings and her alertness, attention span, and communication skills may improve. Many girls remain in this stage for most of their lives.

Stage IV, or the late motor deterioration stage, can last for years or decades. Prominent features include reduced mobility, curvature of the spine (scoliosis) and muscle weakness, rigidity, spasticity, and increased muscle tone with abnormal posturing of an arm, leg, or top part of the body. Girls who were previously able to walk may stop walking. Cognition, communication, or hand skills generally do not decline in stage IV. Repetitive hand movements may decrease and eye gaze usually improves.

Mecp2-deficient mice share several symptoms and characteristics with Rett syndrome patients. MeCP2-deficient mice are hypoactive (Chahrour M and Zoghbi, H Y, Neuron. (2007) 56:422-437; Guy et al., Nat. Genet. (2001) 3:3220326; Chen et al., Nat. Genet. (2001) 3:327-331) and show altered measures of anxiety-related behaviors, e.g., hindlimb clasping. (McGill et al., Proc. Nat. Acad. Sci. (2006) 103: 18267-72) Like their Rett syndrome human counterparts, MeCP2-deficient mice also exhibit abnormal respiration. (Chahrour M and Zoghbi, H Y, Neuron. (2007) 56:422-437; Weese-Mayer et al., Pediatr. Res. (2006) 60:443-449)

VI. Astrocytes

Astrocytes are specialized glial cells that perform many essential complex functions in the healthy CNS, including regulation of blood flow, fluid/ion/pH/neurotransmitter homeostasis, synapse formation/function, energy and metabolism, and blood-brain barrier maintenance (Barres B. A. (2008) Neuron 60:430-440.) While neurons have the highest level of MeCP2 expression, astrocytes and other cell types also express detectable levels of MeCP2. Recent studies suggest that astrocytes likely contribute to the progression of Rett syndrome. (See McGann et al., Curr Opin Neurobiol. 2012 October; 22(5): 850-858). Many studies suggest that the function of astrocytes is impaired by MeCP2 defects. (Maezawa et al., J Neurosci. 2009 Apr. 22; 29(16): 5051-5061). Although MeCP2 levels are roughly five-fold lower in astrocytes than in neurons (Skene et al. Mol Cell (2010) 37:457-468; Maezawa et al. Neurosci (2009) 29:5051-5061), recent studies suggest that loss of MeCP2 in astrocytes contributes to Rett-like symptoms and restoration of MeCP2 can rescue some of these defects (Lioy et al., Nature (2011) 475:497-500). Given their central role in Rett syndrome, there is a significant need to identify and rigorously test new molecular targets that restore normal astrocyte function to effectively slow or even reverse progression of the disorder. There are several potential pathways through which astrocytes can impact the pathology of Rett syndrome.

Astrocytes and Rett Syndrome.

Global re-expression of MeCP2 postnatally in Mecp2-deficient mice results in normal longevity, rescues motor behaviors, and improves overall health. Guy et al., Science. (2007) 315: 1143-1147. Because expression of MeCP2 from the neuronal tau locus in early development prevents appearance of several Rett-like symptoms (Luikenhuis et al., Proc. Nat. Acad. Sci. (2004) 101: 6033-6038), neurons likely play a crucial role in a rescue. However, in vitro studies indicate that astrocytic MeCP2 supports normal neuronal morphology (Maezawa et al., J. Neurosci. (2009) 29: 505105056; Ballas et al., Nat. Neurosci. (2009) 12: 311-317). Therefore, it is likely that astrocytes also play a role in rescuing Rett neuropathology in vivo.

During normal development, neurogenesis takes place first and the changeover to astrogenesis is strictly regulated. While neurogenesis occurs, MeCP2 attaches to methylated portions of astrocyte-specific gene promoters, such as Glial fibrillary acidic protein (GFAP), the hallmark intermediate filament protein in astrocytes. As neural development proceeds, there is a reduction in this methylation and MeCP2 no longer attaches to the promoter, allowing for gene transcription. This controlled timing leads to the generation of the correct number of neurons and astrocytes. However, in Rett syndrome, the changeover to astrogenesis takes place very rapidly since Mecp2 is mutated and does not have the ability to remodel the chromatin of the promoters into an inactive state. Hence, there are chances of a very early transcription of astrocyte genes. It has been observed that induced pluripotent stem cells (iPSCs) in Rett syndrome patients differentiate more readily into GFAP-positive cells when compared to controls, which is further confirmed by a rise in GFAP staining in Rett syndrome brains. (Axol Bioscience Ltd. (2020, February 18). Studying Astrocytes in Rett Syndrome. News-Medical. Retrieved on Jun. 9, 2020 from https://www.news-medical.net/whitepaper/20191112/Studying-Astrocytes-in-Rett-Syndrome.aspx).

Under control conditions, dendritic growth is boosted by healthy astrocytes when co-cultured with healthy neurons. However, co-cultures of astrocytes from Mecp2$^{-/+}$ mice and healthy hippocampal neurons leads to shorter dendrites and somas. In addition, it has been observed that siRNAs targeted against MeCP2 in healthy astrocytes also leads to a decrease in dendritic outgrowth, confirming that this impact is due to the MeCP2 deficiency in astrocytes. (Axol Bioscience Ltd, Ibid.)

The morphology of wild type iPSC-derived interneurons in culture is detrimentally affected by human iPSC-derived astrocytes from Rett syndrome patients; however, in comparison to cultures with Rett syndrome astrocytes, healthy iPSC-derived astrocytes had a positive effect on Rett syndrome iPSC-derived interneurons. This further underscores the effect astrocytes can have on neurons in disease. (Axtol Biosciences, Ibid.)

Lioy et al. reported that removal of Mecp2 just from astrocytes, at postnatal day 21, results in a subtler phenotype than global removal in null mice, and re-expression in astrocytes mainly stabilizes symptoms. (Nature (2012) 475 (7357): 497-500) Others have reported the appearance of a subset of phenotypes after embryonic removal of Mecp2 from subsets of neurons, (Chen et al., Nat. Genet. (2001) 3:327-33 Gemelli et al., Biol, Psych. (2006) 59:468-476), which might be explained by causing disease initiation, and prevention of Rett-like phenotype after Mecp2 re-expression in embryonic neurons (Luikenhuis et al, Proc. Nat. Acad. Sri. (2004) 101:6033-6038). These studies suggest that changes in Mecp2 expression and the pathways it controls over time can modulate the disease phenotype.

Reintroducing Merp2 particularly into astrocytes leads to amelioration of symptoms in Alecp2 null mice (Lim et al., Nature (2012) 475(7357): 497-500). Moreover, astrocyte-conditioned media has been shown to have an advantageous effect on Mecp2$^{-/-}$ murine neurons, enhancing their dendritic length. (Axol Bioscience Ltd, Ibid) These studies demonstrate that by targeting astrocytes, some of the negative impacts in Rett syndrome models can be minimized.

VII. Treatment Methods Using Therapeutic Anti-SEMA4D Antibodies

Methods of the disclosure are directed to the use of anti-SEMA4D binding molecules, e.g., antibodies, including antigen-binding fragments, variants, and derivatives thereof, to treat a subject having Rett syndrome. In certain embodiments the endothelial cells express a SEMA4D receptor, in others the neuronal cells express a SEMA4D receptor, and in others both endothelial and neuronal cells express a SEMA4D receptor. In certain embodiments the receptor is Plexin-B1. Though the following discussion refers to administration of an anti-SEMA4D antibody, the methods described herein are also applicable to the antigen-binding fragments, variants, and derivatives of these anti-SEMA4D antibodies or other biologics or small molecules that retain the desired properties of the anti-SEMA4D antibodies of the disclosure, e.g., capable of specifically binding SEMA4D, e.g., human, mouse, or human and mouse SEMA4D, having SEMA4D neutralizing activity, and/or blocking the interaction of SEMA-4D with its receptor, e.g., Plexin-B1. In another embodiment, the methods refer to administration of an anti-SEMA4D antibody, the methods described herein can also refer to the administration of anti-Plexin-B1 or anti-Plexin-B2 binding molecules that are capable of specifically binding Plexin-B1 and/or Plexin-B2 and blocking the interaction of SEMA-4D with one or both of its Plexin receptors, e.g., Plexin-B1 and/or Plexin-B2.

In one embodiment, treatment includes the application or administration of an anti-SEMA4D binding molecule, e.g., an antibody or antigen binding fragment thereof or other biologic or small molecule that binds and neutralizes SEMA4D as described herein to a patient, where the patient has Rett syndrome, e.g., the patient has symptoms or has the risk of developing symptoms of Rett syndrome. In another embodiment, treatment is also intended to include the application or administration of a pharmaceutical composition comprising the anti-SEMA4D binding molecule, e.g., an antibody or antigen binding fragment thereof to a patient, where the patient has, or has the risk of developing symptoms of Rett syndrome.

The anti-SEMA4D binding molecules, e.g., antibodies or binding fragments thereof as described herein are useful for the treatment of various symptoms of Rett syndrome. In some embodiments, treatment is intended to induce an improvement in the symptoms associated with the disorder. In other embodiments, treatment of Rett syndrome is intended to reduce, retard or stop an increase in symptom manifestations. In other embodiments, treatment of Rett syndrome is intended to inhibit, e.g., suppress, retard, prevent, stop, or reverse a manifestation of symptoms. In other embodiments, treatment of Rett syndrome is intended to relieve to some extent one or more of the symptoms associated with the disorder. In these situations, the symptoms can be neuropsychiatric symptoms, cognitive symptoms, and/or motor dysfunction. In other embodiments, treatment of Rett syndrome is intended to reduce respiratory symptoms. In other embodiments, treatment of is intended to improve quality of life.

In one embodiment, the disclosure relates to the use of anti-SEMA4D binding molecules, e.g., antibodies or antigen-binding fragments, variants, or derivatives thereof, as a medicament, in particular for use in the treatment of Rett syndrome to improve, reduce, or reverse one or more of the symptoms associated with Rett syndrome.

In accordance with the methods of the present disclosure, at least one anti-SEMA4D binding molecule, e.g., an antibody or antigen binding fragment, variant, or derivative thereof, or other biologic or small molecule as defined elsewhere herein can be used to promote a positive therapeutic response with respect to Rett syndrome. A "positive therapeutic response" with respect to Rett syndrome is intended to include an improvement in the symptoms associated with the disorder in symptomatic subjects and is also intended to include prevention and/or improvement of symptoms in asymptomatic subjects or during early onset (Stage I) of the disorder. Such positive therapeutic responses are not limited to the route of administration and can comprise administration to the donor, the donor tissue (such as for example organ perfusion), the host, any combination thereof, and the like. In particular, the methods provided herein are directed to inhibiting, preventing, reducing, alleviating, or lessening the progression of Rett syndrome in a patient. Thus, for example, an improvement in the disorder can be characterized as an absence of some or all clinically observable symptoms, a decrease in the incidence of some or all clinically observable symptoms, or a change in some or all of the clinically observable symptoms.

Activities that change the symptoms associated with Rett syndrome can be detected and measured using in vivo mouse models. In certain embodiments, a Mecp2 mouse model can be employed. The mise incorporate mutations in Mecp2 that are characteristic of Rett syndrome. The Mecp2 mouse model displays some of the primary pathologies associated with the various stages of Rett syndrome: anxiety, repetitive movements similar to hand wringing, e.g., hindlimb clasping, respiratory issues, e.g., apnea, or irregular breathing patterns, memory impairment and muscle tone and motor deficits. It should be appreciated that people skilled in the art will recognize that other models have been described and usefully employed for studies of disease mechanisms and treatment of symptoms in Rett syndrome in the literature and that the present disclosure should not be limited to any one particular model.

The anti-SEMA4D binding molecules, e.g., antibodies or antigen binding fragments, variants, or derivatives thereof or other biologics or small molecules can be used in combination with at least one or more other treatments for Rett syndrome; where the additional therapy is administered prior to, during, or subsequent to administration of the anti-SEMA4D binding molecule, e.g., antibody or antigen binding fragment, variant, or derivative thereof, therapy. Thus, where the combined therapies comprise administration of an anti-SEMA4D binding molecule, e.g., an antibody or antigen binding fragment, variant, or derivative thereof, in combination with administration of another therapeutic agent, the methods of the disclosure encompass coadministration, using separate formulations or a single pharmaceutical formulation, with simultaneous or consecutive administration in either order.

VIII. Pharmaceutical Compositions and Administration Methods

Methods of preparing and administering anti-SEMA4D binding molecules, e.g., antibodies, or antigen-binding fragments, variants, or derivatives thereof to a subject in need thereof are well known to or are readily determined by those skilled in the art. The route of administration of the anti-SEMA4D binding molecule, e.g, antibody, or antigen-binding fragment, variant, or derivative thereof, can be, for example, oral, parenteral, intrathecal, Intracerebroventricular injection or by inhalation or topical administration. The term parenteral as used herein includes, e.g., intravenous, intraarterial, intraperitoneal, intramuscular, subcutaneous, rectal, or vaginal administration. While all these forms of administration are clearly contemplated as being within the scope of the disclosure, an example of a form for administration would be a solution for injection, in particular for intravenous or intraarterial injection or drip. A suitable pharmaceutical composition for injection can comprise a buffer (e.g. acetate, phosphate or citrate buffer), a surfactant (e.g. polysorbate), optionally a stabilizer agent (e.g. human albumin), etc. However, in other methods compatible with the teachings herein, anti-SEMA4D binding molecules, e.g., antibodies, or antigen-binding fragments, variants, or derivatives thereof can be delivered directly to the site of the adverse cellular population thereby increasing the exposure of the diseased tissue to the therapeutic agent.

As discussed herein, anti-SEMA4D binding molecules, e.g., antibodies, or antigen-binding fragments, variants, or derivatives thereof can be administered in a pharmaceutically effective amount for the in vivo treatment of Rett syndrome. In this regard, it will be appreciated that the disclosed binding molecules can be formulated so as to facilitate administration and promote stability of the active agent. In certain embodiments, pharmaceutical compositions in accordance with the present disclosure comprise a pharmaceutically acceptable, non-toxic, sterile carrier such as physiological saline, non-toxic buffers, preservatives and the like. For the purposes of the instant application, a pharmaceutically effective amount of an anti-SEMA4D binding molecule, e.g., an antibody, or antigen-binding fragment, variant, or derivative thereof, shall be held to mean an amount sufficient to achieve effective binding to a target and to achieve a benefit, e.g., improve the symptoms associated with Rett syndrome.

The pharmaceutical compositions used in this disclosure comprise pharmaceutically acceptable carriers, including, e.g., ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include, e.g., water, alcoholic/aqueous solutions, emulsions or suspensions, including saline and buffered media. In the subject disclosure, pharmaceutically acceptable carriers include, but are not limited to, 0.01-0.1 M, e.g., about 0.05 M phosphate buffer or 0.9% saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives can also be present such as, for example, antimicrobials, antioxidants, chelating agents, and inert gases and the like.

More particularly, pharmaceutical compositions suitable for injectable use include sterile aqueous solutions (where water soluble) or dispersions and sterile powders for the extemporaneous preparation of sterile injectable solutions or dispersions. In such cases, the composition must be sterile and should be fluid to the extent that easy syringability exists. It should be stable under the conditions of manufacture and storage and can be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Suitable formulations for use in the therapeutic methods disclosed herein are described in Remington's Pharmaceutical Sciences (Mack Publishing Co.) 16th ed. (1980).

Prevention of the action of microorganisms can be achieved by various antibacterial and antifungal agents, for example, parabens, chlorobutanol, phenol, ascorbic acid, thimerosal and the like. In many cases, isotonic agents can be included, for example, sugars, polyalcohols, such as mannitol, sorbitol, or sodium chloride. Prolonged absorption of the injectable compositions can be brought about by including in the composition an agent which delays absorption, for example, aluminum monostearate and gelatin.

In any case, sterile injectable solutions can be prepared by incorporating an active compound (e.g., an anti-SEMA4D antibody, or antigen-binding fragment, variant, or derivative thereof, by itself or in combination with other active agents) in the required amount in an appropriate solvent with one or a combination of ingredients enumerated herein, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, methods of preparation include vacuum drying and freeze-drying, which yield a powder of an active ingredient plus any additional desired ingredient from a previously sterile-filtered solution thereof. The preparations for injections are processed, filled into containers such as ampoules, bags, bottles, syringes or vials, and sealed under aseptic conditions according to methods known in the art. Further, the preparations can be packaged and sold in the form of a kit. Such articles of manufacture can have labels or package inserts indicating that the associated compositions are useful for treating a subject suffering from, or predisposed to a disease or disorder.

Parenteral formulations can be a single bolus dose, an infusion or a loading bolus dose followed with a maintenance dose. These compositions can be administered at specific fixed or variable intervals, e.g., once a day, or on an "as needed" basis.

Certain pharmaceutical compositions used in this disclosure can be orally administered in an acceptable dosage form including, e.g., capsules, tablets, aqueous suspensions or solutions. Certain pharmaceutical compositions also can be administered by nasal aerosol or inhalation. Such compositions can be prepared as solutions in saline, employing benzyl alcohol or other suitable preservatives, absorption promoters to enhance bioavailability, and/or other conventional solubilizing or dispersing agents.

The amount of an anti-SEMA4D binding molecule, e.g., antibody, or fragment, variant, or derivative thereof, to be combined with the carrier materials to produce a single dosage form will vary depending upon the host treated and the particular mode of administration. The composition can be administered as a single dose, multiple doses or over an established period of time in an infusion. Dosage regimens also can be adjusted to provide the optimum desired response (e.g., a therapeutic or prophylactic response).

In keeping with the scope of the present disclosure, anti-SEMA4D antibodies, or antigen-binding fragments, variants, or derivatives thereof can be administered to a human or other animal in accordance with the aforementioned methods of treatment in an amount sufficient to produce a therapeutic effect. The anti-SEMA4D antibodies, or antigen-binding fragments, variants or derivatives thereof can be administered to such human or other animal in a conventional dosage form prepared by combining the antibody of the disclosure with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables. Those skilled in the art will further appreciate that a cocktail comprising one or more species of anti-SEMA4D binding molecules, e.g., antibodies, or antigen-binding fragments, variants, or derivatives thereof, of the disclosure can be used.

By "therapeutically effective dose or amount" or "effective amount" is intended an amount of anti-SEMA4D binding molecule, e.g., antibody or antigen binding fragment, variant, or derivative thereof, that when administered brings about a positive therapeutic response with respect to treatment of a patient with Rett syndrome. A positive therapeutic response can alleviate symptoms of the disorder; decrease, reduce, retard or stop the incidence of symptoms; decrease, reduce, retard the severity of symptoms; inhibit, e.g., suppress, retard, prevent, stop, or reverse the manifestation of symptoms; relieve to some extent one or more of the symptoms associated with the disorder; reduce morbidity and mortality; improve quality of life; or a combination of such effects. In certain embodiments, administration of a therapeutically effective dose or amount alleviates, decreases, reduces, retards or stops the incidence of one or more symptoms; decreases, reduces, retards the severity of one or more symptoms; inhibits, e.g., suppresses, retards, prevents, stops, or reverses the manifestation of one or more symptoms wherein the symptoms can include irregular respiratory patterns, hyperventilation, sleep apnea, anxiety, body tremors, repetitive hand movements such as hand wringing, tapping, clasping and the like, difficulties with coordination and/or locomotion, delays in development of fine or gross motor control, decreased gross or fine motor control, decreased cognition, decreased memory, delayed or decreased communication skills, apraxia, muscle weakness, abnormal posturing, seizures, gastrointestinal problems, abnormal cardiorespiratory coupling, decreased bone density, early-onset osteoporosis, bruxism, dyslipidaemia, inflammation of the gallbladder, scoliosis, urological dysfunction, and sleep disturbances, poor quality of life (all as compared to a non-Rett syndrome "normal" subject), and combinations thereof. (See Vashi N and Justice MJ. Mammalian Genome (2019) 30:90-110).

Therapeutically effective doses of the compositions of the present disclosure, for the prevention of occurrence of decrease in the incidence of symptoms, vary depending upon many different factors, including means of administration, target site, physiological state of the patient, pathological stage of the disorder, other medications administered, and whether treatment is prophylactic or therapeutic. Treatment dosages can be titrated using routine methods known to those of skill in the art to optimize safety and efficacy.

The amount of at least one anti-SEMA4D binding molecule, e.g., antibody or binding fragment, variant, or derivative thereof, to be administered is readily determined by one of ordinary skill in the art without undue experimentation given the present disclosure. Factors influencing the mode of administration and the respective amount of at least one anti-SEMA4D binding molecule, e.g., antibody, antigen-binding fragment, variant or derivative thereof include, but are not limited to, the severity of the disorder, the history of the disorder, the stage of the disorder, and the age, height, weight, health, and physical condition of the individual undergoing therapy. Similarly, the amount of anti-SEMA4D binding molecule, e.g., antibody, or fragment, variant, or derivative thereof, to be administered will be dependent upon the mode of administration and whether the subject will undergo a single dose or multiple doses of this agent.

The disclosure also provides for the use of an anti-SEMA4D binding molecule, e.g., antibody of the disclosure, or antigen-binding fragment, variant, or derivative thereof, in the manufacture of a medicament for treating a subject with Rett syndrome. In certain embodiments, the medicament is manufactured for use in a subject in the first clinical stage of Rett syndrome, i.e., Stage I as defined above. In another embodiment, the medicament is manufactured for use in a subject in a later clinical stage of Rett syndrome, e.g., Stage II, Stage III, or Stage IV as defined above. In certain embodiments, the medicament is manufactured for use in a subject that has been pretreated with at least one other therapy. By "pretreated" or "pretreatment" is intended the subject has received one or more other therapies (e.g., been treated with at least one other therapy for one or more symptoms of Rett syndrome) prior to receiving the medicament comprising the anti-SEMA4D binding molecule, e.g., antibody or antigen-binding fragment, variant, or derivative thereof "Pretreated" or "pretreatment" includes subjects that have been treated with at least one other therapy within 2 years, within 18 months, within 1 year, within 6 months, within 2 months, within 6 weeks, within 1 month, within 4 weeks, within 3 weeks, within 2 weeks, within 1 week, within 6 days, within 5 days, within 4 days, within 3 days, within 2 days, or even within 1 day prior to initiation of treatment with the medicament comprising the anti-SEMA4D binding molecule, for example, the monoclonal antibodies VX15/2503, 67, or 76 disclosed herein, or antigen-binding fragment, variant, or derivative thereof. It is not necessary that the subject was a responder to pretreatment with the prior therapy or therapies. Thus, the subject that receives the medicament comprising the anti-SEMA4D binding molecule, e.g., an antibody or antigen-binding fragment, variant, or derivative thereof could have responded, or could have failed to respond, to pretreatment with the prior therapy, or to one or more of the prior therapies where pretreatment comprised multiple therapies.

The practice of the present disclosure will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Sambrook et al., ed. (1989) Molecular Cloning A Laboratory Manual (2nd ed.; Cold Spring Harbor Laboratory Press); Sambrook et al., ed. (1992) Molecular Cloning: A Laboratory Manual, (Cold Springs Harbor Laboratory, NY); D. N. Glover ed., (1985) DNA Cloning, Volumes I and II; Gait, ed. (1984) Oligonucleotide Synthesis; Mullis et al. U.S. Pat. No. 4,683,195; Hames and Higgins, eds. (1984) Nucleic Acid Hybridization; Hames and Higgins, eds. (1984) Transcription And Translation; Freshney (1987) Culture Of Animal Cells (Alan R. Liss, Inc.); Immobilized Cells And Enzymes (IRL Press) (1986); Perbal (1984) A Practical Guide To Molecular Cloning; the treatise, Methods In Enzymology (Academic Press, Inc., N.Y.); Miller and Calos eds. (1987) Gene Transfer Vectors For Mammalian Cells, (Cold Spring Harbor Laboratory); Wu et al., eds., Methods In Enzymology, Vols. 154 and 155; Mayer and Walker, eds. (1987) Immunochemical Methods In Cell And Molecular Biology (Academic Press, London); Weir and Blackwell, eds., (1986) Handbook Of Experimental Immunology, Volumes I-IV; Manipulating the Mouse Embryo, Cold Spring Harbor Laboratory Press, Cold Spring Harbor, N.Y., (1986); and in Ausubel et al. (1989) Current Protocols in Molecular Biology (John Wiley and Sons, Baltimore, Md.).

General principles of antibody engineering are set forth in Borrebaeck, ed. (1995) Antibody Engineering (2nd ed.; Oxford Univ. Press). General principles of protein engineering are set forth in Rickwood et al., eds. (1995) Protein Engineering, A Practical Approach (IRL Press at Oxford Univ. Press, Oxford, Eng.). General principles of antibodies and antibody-hapten binding are set forth in: Nisonoff (1984) Molecular Immunology (2nd ed.; Sinauer Associates, Sunderland, Mass.); and Steward (1984) Antibodies, Their Structure and Function (Chapman and Hall, New York, N.Y.). Additionally, standard methods in immunology known in the art and not specifically described are generally followed as in Current Protocols in Immunology, John Wiley & Sons, New York; Stites et al., eds. (1994) Basic and Clinical Immunology (8th ed; Appleton & Lange, Norwalk, Conn.) and Mishell and Shiigi (eds) (1980) Selected Methods in Cellular Immunology (W.H. Freeman and Co., NY).

Standard reference works setting forth general principles of immunology include Current Protocols in Immunology, John Wiley & Sons, New York; Klein (1982) J., Immunology: The Science of Self-Nonself Discrimination (John Wiley & Sons, NY); Kennett et al., eds. (1980) Monoclonal Antibodies, Hybridoma: A New Dimension in Biological Analyses (Plenum Press, NY); Campbell (1984) "Monoclonal Antibody Technology" in Laboratory Techniques in Biochemistry and Molecular Biology, ed. Burden et al., (Elsevere, Amsterdam); Goldsby et al., eds. (2000) Kuby Immunology (4th ed.; H. Freemand & Co.); Roitt et al. (2001) Immunology (6th ed.; London: Mosby); Abbas et al. (2005) Cellular and Molecular Immunology (5th ed.; Elsevier Health Sciences Division); Kontermann and Dubel (2001) Antibody Engineering (Springer Verlang); Sambrook and Russell (2001) Molecular Cloning: A Laboratory Manual (Cold Spring Harbor Press); Lewin (2003) Genes VIII (Prentice Hall 2003); Harlow and Lane (1988) Antibodies: A Laboratory Manual (Cold Spring Harbor Press); Dieffenbach and Dveksler (2003) PCR Primer (Cold Spring Harbor Press).

All of the references cited above, as well as all references cited herein, are incorporated herein by reference in their entireties.

The following examples are offered by way of illustration and not by way of limitation.

EXAMPLES

Example 1: Testing the Effects of an Anti-SEMA4D Binding Molecule on Symptoms Associated with Rett Syndrome in the Mecp2$^{T158A}$ Rett Syndrome Mouse Model Experimental Design The Mecp2$^{T158A}$ Rett syndrome mouse model was created by Goffin et al. (*Nature Neuroscience* volume 15, pages 274-283(2012)) and closely recapitulates the phenotypic features of the human disorder. Mutations at threonine 158 are the most common Mecp2 mutations observed in Rett syndrome patients and produce highly variable phenotypes in transgenic mice. The Mecp2$^{T158A/y}$ hemizygous male mice (referred to hereinafter as Mecp2 mice) display a range of symptoms at different ages and usually start developing symptoms at 4-6 weeks old. A preclinical trial was conducted on hemizygous Mecp2$^{T158A/y}$ and wild type C57BL/6 male mice.

Hemizygous Mecp2$^{T158A/y}$ and wild type C57BL/6 male mice were treated with either anti-SEM4D (Mab 67) or isotype control monoclonal antibody at 4 weeks old when the Mecp2$^{T158A/y}$ mice were pre-symptomatic or 8 weeks old when the Mecp2$^{T158A/y}$ mice were symptomatic (Table 1). All mice received 50 mg/kg of anti-SEM4D (Mab 67) or isotype control antibody (Mab 2B8 mouse IgG1) by intraperitoneal injection for 10 weeks. The pre-symptomatic mice (4-week cohort; "4-weekers") and 4-weeker controls were injected twice weekly, while the symptomatic mice (8-week cohort; "8-weekers") and 8-weeker controls were dosed twice weekly in the first four weeks and once weekly between weeks 5-10 of the trial.

TABLE 1

Experimental plan for the preclinical trial.

| Mouse Group | Age of Start of Treatment | Treatment Type | Treatment Duration | N= |
|---|---|---|---|---|
| Wild type | 4 weeks old | Isotype control | 10 weeks | 10 |
| Pre-symptomatic Mecp2$^{T158A/y}$ | 4 weeks old | Isotype control | 10 weeks | 11 |
| Pre-symptomatic Mecp2$^{T158A/y}$ | 4 weeks old | Anti-SEMA4D | 0 weeks | 11 |
| Wild type | 8 weeks old | Isotype control | 10 weeks | 10 |
| Symptomatic Mecp2$^{T158A/y}$ | 8 weeks old | Isotype control | 10 weeks | 12 |
| Symptomatic Mecp2$^{T158A/y}$ | 8 weeks old | Anti-SEMA4D | 10 weeks | 10 |

Phenotypic scoring was performed on a weekly basis for the severity of RTT-specific symptoms including tremor and hindlimb clasping according to the criteria in Table 2. Every two weeks, coordination, locomotion, cognition and respiratory pattern measures were assessed using the rotarod, elevated plus maze, and whole body plethysmography tests. These behavioral tests were conducted over 3-4 days to reduce anxiety and fatigue in the mice. The mice were weighed once a week.

TABLE 2

Scoring criteria for Rett syndrome-specific symptoms in Mecp2$^{T158A}$ mice.

| Score | Tremor | Hindlimb Clasping |
|---|---|---|
| 0 | Not visible or sensible when held in Hands | Hindlimbs consistently splayed outward, away from the abdomen |
| 1 | Not visible but sensible when held in hands | One hindlimb retracted or both hindlimbs partially retracted toward the abdomen |
| 2 | Visible and sensible when held in hands | Hindlimbs entirely retracted and touching the abdomen |

Figure 1:
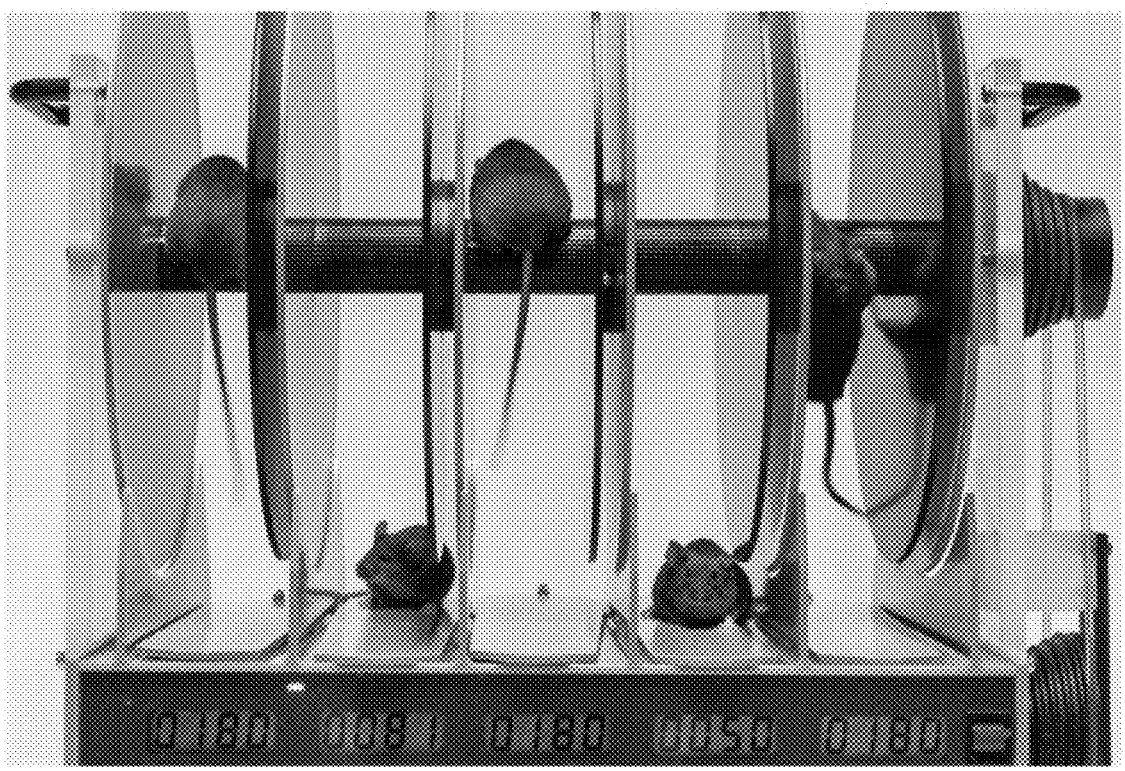
FIG. 1 shows an accelerating rotarod apparatus used for behavioral testing.

Rotarod. Mice were placed on an accelerating rotarod apparatus (FIG. 1) for 3 trials with at least 15 minutes of rest between the trials. Each trial lasted for a maximum of 3 minutes, during which the rod accelerated 5 rpm every 15 seconds from 5 to 6 rpm. The latency to fall from the rod was recorded for each trial.

Figure 2:
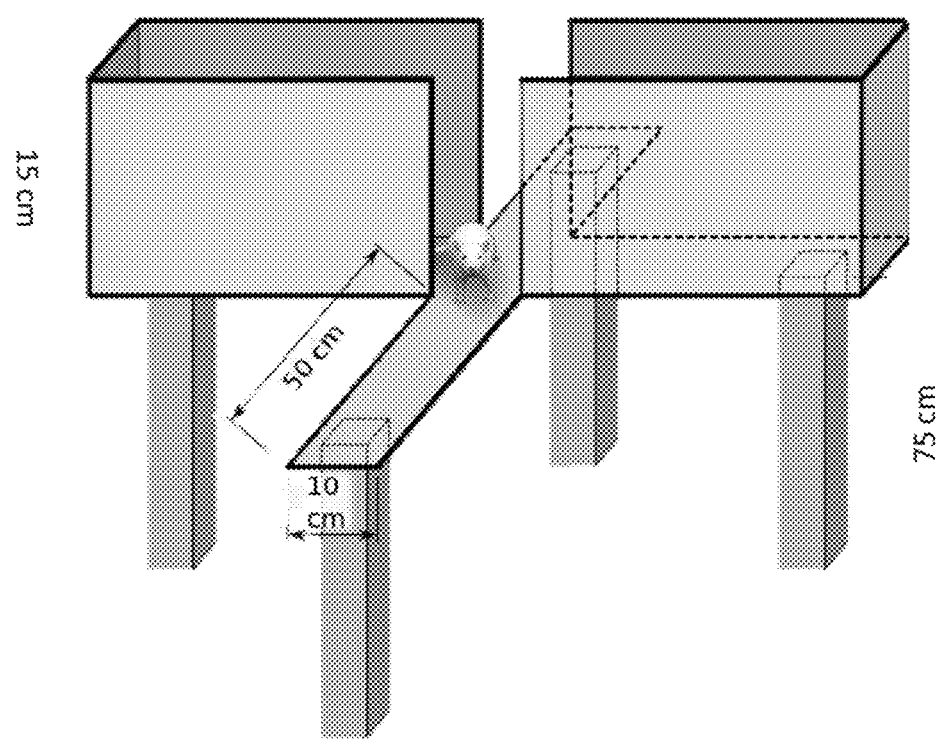
FIG. 2 shows an elevated plus maze apparatus for behavioral testing.

Elevated Plus Maze. Each mouse was placed in the cross section of the elevated plus maze apparatus (FIG. 2) for 5 minutes as previously published (Komada et al., 2008, Vis. Exp., December 22 (22): 1088). The time spent in the closed and open arms and the numbers of entry into closed and open arms were recorded.

Figure 3:
FIG. 3 shows a whole body plethysmography apparatus for testing respiration patterns.

Whole Body Plethysmography. Each mouse sat in a chamber of the whole body plethysmography apparatus (FIG. 3) in a dark room for 3 hours without disturbance. The breathing pattern (Table 3) of each animal was recorded and analyzed by EMKA iox software.

TABLE 3

Parameters measured in whole body plethysmography test.

| Parameter | Unit | Description |
| --- | --- | --- |
| Inspiratory Time (Ti) | Ms | Time from start of inspiration to end of inspiration. |
| Expiratory Time (Te) | Ms | Time from start of expiration to beginning of next inspiration. |
| Peak Inspiratory Flow (PIF) | ml/s | The maximum negative flow during one breath. |
| Peak Expiratory Flow (PEF) | ml/s | The maximum positive flow during one breath. |
| Tidal Volume (TV) | Ml | The integral of the flow during inspiration (negative period). |
| Expired Volume (EV) | Ml | The integral of the flow during expiration (positive period). |
| Relaxation Time (RT) | Ms | The time it takes to expire a user-defined percentage of tidal volume. |
| Minute Volume (MV) | Ml | The total volume breathed over one minute based on current breathing rate. |
| Period (P) | Ms | The time interval between two beats. |
| Frequency of breathing (f) | Bpm | The breath-by-breath rate of breathing. |
| End-Inspiratory Pause (EIP) | Ms | The pause between end of inspiration and start of expiration. |
| End-Expiratory Pause (EEP) | Ms | The pause that follows expiration (apnoea). |
| Accumulated Volume (AV) | Ml | Sum of tidal volume. Updated during storage and restored at each storage start. |

Following the conclusion of behavioral testing, mice were sacrificed, and brain tissues were processed for formalin-fixed paraffin-embedded (FFPE) immunohistochemistry. For all tests, statistical analysis was performed using the 2-way ANOVA test with repeated measures.

Analysis of 4-Week Old Pre-Symptomatic Mice (4-Weekers).

Anti-SEMA4D Improves Hindlimb Clasping Phenotype and Decreases Body Tremors in Pre-symptomatic Mice.

Hindlimb clasping in Mecp2 mice is a postural response that resembles the characteristic hand wringing stereotypies present in Rett syndrome patients. Phenotypic hindlimb clasping of Mecp2 mice is shown in FIG. 4A. Scoring criteria ranging from 0 to 2 as outlined in Table 2 was used to assess the severity of hindlimb clasping. Hindlimb clasping in pre-symptomatic mice that received isotype control antibody progressively worsened throughout the 10-week study, reaching a score of ~1.8. In contrast, hindlimb clasping in the anti-SEMA4D treated mice peaked at three weeks (score of ~1.1) and declined for two weeks, finally plateauing at a score of ~0.75 for the remainder of the study. Wild type mice exhibited no hindlimb clasping throughout the study. (FIG. 4B)

Body tremors is one of the many symptoms of Rett syndrome in humans. Mecp2 mice develop tremors as the disorder progresses. Scoring criteria ranging from 0 to 2 as outlined in Table 2 was used to assess the severity of whole body tremors throughout the 10 week study. Body tremors in pre-symptomatic mice that received isotype antibody control progressively worsened from week 1 to week 8, eventually leveling off at a score of ~1.6 to 1.7. Tremors in anti-SEMA4D treated Mecp2 mice progressed at the same level as isotype control mice for the first four weeks of treatment to a score of ~1 and then decreased to a score of −0.75 throughout the rest of the 10-week study. Wild type mice exhibited no tremors throughout the 10-week study. (FIG. 5) These results indicate that anti-SEMA4D antibody treatment improves the characteristic posturing stereotypes of Rett syndrome in the pre-symptomatic stage of the disorder, as well as reducing the body tremors associated with this stage of the disorder.

Anti-SEMA4D Improves Coordination and Locomotion in Pre-symptomatic Mice.

Over time, children with Rett syndrome have increasing problems with the use of muscles that control movement, coordination and communication. Mecp2 mice exhibit similar problems with coordination and locomotion.

Four-week old mice were tested for locomotion and coordination on a rotarod apparatus as described above. The results are shown in FIG. 6. As can be seen, the isotype antibody-treated Mecp2 mice failed to improve after the first week, with locomotion and coordination worsening after week three. In contrast, the anti-SEMA4D-treated Mecp2 mice retained initial coordination and locomotion, showing a measurable improvement during the course of the study, although not to the same extent as wild type mice.

Anti-SEMA4D Prevents or Decreases Cognition Loss in Pre-symptomatic Mice.

The elevated plus maze (EPM) test uses an elevated, plus-shaped (+) apparatus with two open and two enclosed arms. The behavioral model is based on the general aversion of mice to open spaces. This aversion is expressed as a preference for remaining in enclosed spaces or close to the edges of a bounded space, which translates into the animals limiting their movement to the enclosed arms of the apparatus. Anxiety reduction is indicated in the elevated plus-maze by an increase in the proportion of time spent in the open arms (time in open arms/total time in open or closed arms) and an increase in the proportion of entries into the open arms (entries into open arms/total entries into open or closed arms). The total number of arm entries and number of closed-arm entries are used as measures of general activity.

In the present study, the EPM was used to determine how impaired cognition due to a deficiency in the Mecp2 protein could affect the behavior of mice in the EPM task and whether treatment with anti-SEMA4D affects cognition in impaired mice. Each mouse in the wild type, isotype antibody-treated control and anti-SEMA4D treated cohorts was placed in the cross section of an elevated plus maze apparatus (FIG. 2) for 5 minutes. The time spent in the closed and open arms and the numbers of entry into closed and open arms were recorded. The Mecp2 mice demonstrated no deficit in cognition at the start of the study, and within the first three weeks of testing, the anti-SEMA4D-treated Mecp2 mice demonstrated a recognition of the aversive properties of the open arms, as did the wild type mice. In contrast, isotype antibody-treated control Mecp2 mice were unable to learn the aversive properties of the open arms of EPM. Wild-type mice and anti-SEMA4D treated Mecp2 mice spent significantly less and decreasing amounts of time in the open arms than isotype antibody-treated Mecp2 mice (FIG. 7A) and also demonstrated recognition of the danger of the open arms by making fewer entries into the open arms in comparison to the isotype antibody treated mice. (FIG. 7B) These results show that the anxiolytic-like behaviour of MeCP2 mice is not just related to levels of innate anxiety but also to their inability to recognize potential danger associated with the open arms of the EPM task. Treatment with anti-SEMA4D antibody maintained the pre-symptomatic Mecp2 mice's cognition, enabling the mice to recognize and avoid the potential danger of the open arms.

These results demonstrate that anti-SEMA4D treatment during the pre-symptomatic period of the disorder maintains cognition, i.e., prevents decreases in cognition observed in untreated Mecp2 mice.

Anti-SEMA4D Improves the Respiratory Pattern of Pre-symptomatic Mice.

RTT patients present with a complex respiratory phenotype that can include periods of hyperventilation, apnea, breath holds terminated by Valsalva maneuvers, forced and deep breathing and apneustic breathing, as well as abnormalities of heart rate control and cardiorespiratory integration. Severely arrhythmic breathing is a hallmark of Rett syndrome and profoundly affects quality of life for patients and their families.

Recent studies of mouse models of RTT have shed light on neurologic deficits that likely contribute to respiratory dysfunction including, in particular, defects in neurochemical signaling resulting from abnormal patterns of neurotransmitter and neuromodulator expression. To determine whether blocking SEMA4D signaling in Mecp2 mice can affect the respiratory patterns of Rett syndrome subjects, Mecp2 mice were subjected to whole body plethysmography, as described above. As shown in FIGS. 8A and B, anti-SEMA4D-treated mice exhibited a respiratory pattern (both inspiratory and expiratory) similar to that of wild type mice. The isotype antibody-treated Mecp2 mice exhibited an irregular respiratory pattern, with lower inspiratory and expiratory times compared to anti-SEMA4D-treated Mecp2 mice. These data demonstrate that anti-SEMA4D treatment can prevent respiratory irregularities associated with Rett syndrome.

Analysis of 8-Week Old Symptomatic Mice (8-Weekers).

Anti-SEMA4D Improves Hindlimb Clasping Phenotype and Decreases Body Tremors in Symptomatic Mice.

The scoring criteria ranging from 0 to 2 as outlined in Table 2 was used to assess the severity of hindlimb clasping in wild type, and control-treated and anti-SEMA4D treated 8-week old symptomatic Mecp2 mice over a period of ten weeks. Hindlimb clasping in symptomatic mice that received isotype control antibody progressively worsened throughout the 10-week study, reaching a score of −1.8, similar to that of the isotype control pre-symptomatic mice (FIG. 5B). In contrast, hindlimb clasping in the anti-SEMA4D treated mice was at its highest at the start of testing (score of −1.4) and decreased and remained below that level for the duration of testing. Wild type mice exhibited no hindlimb clasping throughout the study. (FIG. 9)

The scoring criteria ranging from 0 to 2 as outlined in Table 2 was used to assess the severity of whole body tremors throughout a 10 week study of symptomatic Mecp2 mice. Body tremors in symptomatic mice that received isotype antibody control progressively worsened from week 1 to week 10, eventually leveling off at a score of −1.8. Tremors in anti-SEMA4D treated Mecp2mice decreased progressively until week five and then leveled off at a score of less than 1, i.e., less than half that of the isotype antibody control mice. Wild type mice exhibited no tremors throughout the 10-week study. (FIG. 10)

These results indicate that anti-SEMA4D antibody treatment improves the characteristic posturing stereotypes of Rett syndrome in the symptomatic stage of the disorder, as it does in the pre-symptomatic stage of the disorder and significantly reduces body tremors regardless of whether administered during the pre-symptomatic or symptomatic stage of the disorder.

Anti-SEMA4D Improves Coordination and Locomotion in Symptomatic Mecp2 Mice.

To determine whether treatment with anti-SEMA4D antibody affects coordination and locomotion if administered after issues with muscle control develop, symptomatic mice and controls were tested on an accelerating rotarod apparatus. Symptomatic mice (8-weekers) were placed on an accelerating rotarod apparatus every two weeks for 3 trials with at least 15 minutes of rest between the trials, as described above. The results are shown in FIG. 11. As can be seen, the isotype antibody-treated Mecp2 mice failed to improve after the first week, with locomotion and coordination worsening during the test period. In contrast, the anti-SEMA4D-treated Mecp2 mice improved significantly during the course of the study, even surpassing the skill level of the wild type mice who retained a relatively steady level of skill throughout testing.

Anti-SEMA4D Increases Cognition in Symptomatic Mice.

The EPM was used to determine whether treatment of symptomatic mice (8-weekers) with anti-SEMA4D affects cognition in impaired mice. Each mouse in the wild type, isotype antibody-treated control and anti-SEMA4D treated cohorts was placed in the cross section of an elevated plus maze apparatus (FIG. 2) for 5 min. The time spent in the closed and open arms and the numbers of entry into closed and open arms were recorded. Wild-type mice demonstrated a recognition of the aversive properties of the open arms, as did the anti-SEMA4D-treated Mecp2 mice, whereas isotype antibody-treated control Mecp2 mice were unable to learn the aversive properties of the open arms of EPM. As was shown with the pre-symptomatic mice, wild-type mice and anti-SEMA4D treated Mecp2mice spent significantly less and decreasing amounts of time in the open arms than isotype antibody-treated Mecp2 mice (FIG. 12A) and also demonstrated recognition of the danger of the open arms by making fewer entries into the open arms in comparison to the isotype antibody treated mice. (FIG. 12B). These results show that the treatment of symptomatic mice with anti-SEMA4D antibody increases cognition just as anti-SEMA4D treatment prevents cognition decline in pre-symptomatic mice.

Anti-SEMA4D Improves the Respiratory Pattern of Symptomatic Mice.

To determine whether blocking SEMA4D signaling has a positive effect on the respiratory patterns of symptomatic subjects, anti-SEMA4D-treated, control Mecp2 and wild type mice were subjected to whole body plethysmography, as described above. Briefly, wild type, anti-SEMA4D-treated Mecp2 mice and isotype antibody-treated Mecp2 mice were placed in a chamber of the whole body plethysmography apparatus shown in FIG. 3 in a dark room for 3 hours without disturbance. The breathing pattern (Table 3) of each animal was recorded and analyzed by EMKA iox software.

As shown in FIGS. 13A and B, anti-SEMA4D-treated mice exhibited an improved respiratory pattern (both inspiratory and expiratory) after three weeks of treatment, which approached that of wild type mice. The isotype antibody-treated MeCP2 mice exhibited an irregular respiratory pattern, with both lower inspiratory and expiratory times compared to anti-SEMA4D-treated Mecp2 mice.

These data demonstrate that anti-SEMA4D treatment can improve respiratory irregularities after onset of respiratory symptoms.

Table 4 below summarizes the results of the studies reported above.

TABLE 4

|  | 4-Weekers Pre-symptomatic | 8-Weekers Symptomatic |
|---|---|---|
| Lifespan | No change | No change |
| Body Weight | No change | No change |
| Rett-specific Symptoms Tremors and Hindlimb Clasping (Posturing) | Improved from week 5 | Improved from week 3 |
| Rotarod Coordination and Locomotion | Improved from week 3 | Improved from week 3 |
| Elevated Plus Maze Anxiety/Cognition | Prevented from deficit | Improved from week 5 |
| Whole Body Plethysmography Respiration | Prevented from deficit | Improved from week 3 |

SEMA4D Is Upregulated in Neurons of Rett Mice

Formalin fixed paraffin embedded sections of brains from ~8 month old female mice (Mecp2$^{T158A}$ and wild type littermate controls C57BL/6) were stained for SEMA4D (CD100 Polyclonal Antibody-Invitrogen-PA5-47711) and neuronal marker HuC/HuD. (Monoclonal Antibody (16A11)-Invitrogen: A-21271). Representative images of hippocampus regions are shown in FIG. 14. As can be seen, SEMA4D is significantly upregulated in neurons of the Rett mice, while there is no difference in expression of the neuronal marker HuC/HuD in Rett mice compared to wild type controls.

What is claimed is:

1. A method of alleviating symptoms in a subject having Rett syndrome, comprising administering to the subject an effective amount of an isolated antibody or antigen-binding fragment thereof which specifically binds to semaphorin-4D (SEMA4D), wherein the antibody or fragment thereof comprises (1) a variable heavy chain (VH) comprising VH CDRs 1-3 comprising SEQ ID NOs: 3, 4, and 5, respectively, and a variable light chain (VL) comprising VL CDRs 1-3 comprising SEQ ID NOS: 8, 9, and 10, respectively; or (2) a variable heavy chain (VH) comprising VHCDRs 1-3 comprising SEQ ID NOs: 22, 23, and 24, respectively, and a variable light chain (VL) comprising VLCDRs 1-3 comprising SEQ ID NOs: 26, 27, and 28, respectively.

2. The method of claim 1, wherein the antibody or antigen-binding fragment thereof inhibits SEMA4D interaction with a receptor or a portion of a receptor for SEMA4D.

3. The method of claim 2, wherein the receptor is selected from the group consisting of Plexin-B1, Plexin-B2, and CD72.

4. The method of claim 1, wherein the antibody or antigen-binding fragment thereof inhibits SEMA4D receptor-mediated signal transduction.

5. The method of claim 1, wherein the antibody or antigen-binding fragment thereof comprises a variable heavy chain (VH) comprising VHCDRs 1-3 comprising SEQ ID Nos 3, 4, and 5, respectively and a variable light chain (VL) comprising VLCDRs 1-3 comprising SEQ ID NOs: 8, 9, and 10, respectively.

6. The method of claim 5, wherein the VH and VL comprise, respectively, have an amino acid sequence at least 80%, 85%, 90%, 95%, or 100% identical to SEQ ID NO: 6 and/or an amino acid sequence at least 80%, 85%, 90%, 95%, or 100% identical to SEQ ID NO: 11; or an amino acid sequence at least 80%, 85%, 90%, 95%, or 100% identical to SEQ ID NO: 7 and/or an amino acid sequence at least 80%, 85%, 90%, 95%, or 100% identical to SEQ ID NO: 12.

7. The method of claim 1, wherein the antibody or antigen-binding fragment thereof comprises a variable heavy chain (VH) comprising VHCDRs 1-3 comprising SEQ ID Nos 22, 23, and 24, respectively, and a variable light chain (VL) comprising VLCDRs 1-3 comprising SEQ ID NOs 26, 27, and 28, respectively.

8. The method of claim 7, wherein the VH and VL comprise, respectively, an amino acid sequence at least 80%, 85%, 90%, 95%, or 100% identical to SEQ ID NO: 21 and/or an amino acid sequence at least 80%, 85%, 90%, 95%, or 100% identical to SEQ ID NO: 25.

9. The method of claim 1, wherein the subject is in Stage 1 of Rett syndrome.

10. The method of claim 9, wherein the Rett syndrome Stage 1 symptoms comprise one or more symptoms selected from the group consisting of neuropsychiatric symptoms, cognitive symptoms, motor dysfunction, delayed physical development, delayed communication development, loss of communication skills, sleep disturbances, irregular heartbeat, irregular breathing patterns, repetitive jerky movements, and body tremors.

11. The method of claim 10, wherein alleviating symptoms comprises preventing or reducing anxiety-like behaviour, increasing cognition, increasing coordination, increasing locomotion, progressing physical development, decreasing body tremors, decreasing repetitive movements, increasing motor skills, increasing communication skills, decreasing sleep disturbances, decreasing agitation, decreasing restlessness, decreasing breathing irregularities, and any combination thereof.

12. The method of claim 1, wherein the subject is in Stage II, Stage III, or Stage IV of Rett syndrome.

13. The method of claim 12, wherein the symptoms are selected from the group consisting of neuropsychiatric symptoms, cognitive symptoms, delayed physical development, motor dysfunction, irregular heartbeat and breathing, decreased communication skills, scoliosis, sleep disturbances, seizures, gastrointestinal problems, repetitive jerky motions, body tremors, and any combination thereof.

14. The method of claim 13, wherein alleviating symptoms comprises reducing anxiety-like behaviour, increasing cognition, increasing coordination, increasing locomotion, progressing physical development, decreasing body tremors, decreasing repetitive motions, increasing motor skills, increasing communication skills, or any combination thereof.

15. The method of claim 5, wherein the VH and VL comprise, respectively, SEQ ID NO: 6 and SEQ ID NO: 11 or SEQ ID NO: 7 and SEQ ID NO: 12.

16. The method of claim 8, wherein the VH and VL comprise, respectively, SEQ ID NO: 21 and SEQ ID NO: 25.

* * * * *

SEQUENCE LISTING

```
<160> NUMBER OF SEQ ID NOS: 28

<210> SEQ ID NO 1
<211> LENGTH: 862
<212> TYPE: PRT
<213> ORGANISM: Homo sapiens
<220> FEATURE:
<223> OTHER INFORMATION: HUMAN semaphorin-4D

<400> SEQUENCE: 1

Met Arg Met Cys Thr Pro Ile Arg Gly Leu Leu Met Ala Leu Ala Val
1               5                   10                  15

Met Phe Gly Thr Ala Met Ala Phe Ala Pro Ile Pro Arg Ile Thr Trp
            20                  25                  30

Glu His Arg Glu Val His Leu Val Gln Phe His Glu Pro Asp Ile Tyr
        35                  40                  45

Asn Tyr Ser Ala Leu Leu Leu Ser Glu Asp Lys Asp Thr Leu Tyr Ile
    50                  55                  60

Gly Ala Arg Glu Ala Val Phe Ala Val Asn Ala Leu Asn Ile Ser Glu
65                  70                  75                  80

Lys Gln His Glu Val Tyr Trp Lys Val Ser Glu Asp Lys Lys Ala Lys
                85                  90                  95

Cys Ala Glu Lys Gly Lys Ser Lys Gln Thr Glu Cys Leu Asn Tyr Ile
            100                 105                 110

Arg Val Leu Gln Pro Leu Ser Ala Thr Ser Leu Tyr Val Cys Gly Thr
        115                 120                 125

Asn Ala Phe Gln Pro Ala Cys Asp His Leu Asn Leu Thr Ser Phe Lys
    130                 135                 140

Phe Leu Gly Lys Asn Glu Asp Gly Lys Gly Arg Cys Pro Phe Asp Pro
145                 150                 155                 160

Ala His Ser Tyr Thr Ser Val Met Val Asp Gly Glu Leu Tyr Ser Gly
                165                 170                 175

Thr Ser Tyr Asn Phe Leu Gly Ser Glu Pro Ile Ile Ser Arg Asn Ser
            180                 185                 190

Ser His Ser Pro Leu Arg Thr Glu Tyr Ala Ile Pro Trp Leu Asn Glu
        195                 200                 205

Pro Ser Phe Val Phe Ala Asp Val Ile Arg Lys Ser Pro Asp Ser Pro
    210                 215                 220
```

-continued

```
Asp Gly Glu Asp Asp Arg Val Tyr Phe Phe Thr Glu Val Ser Val
225                 230                 235                 240

Glu Tyr Glu Phe Val Phe Arg Val Leu Ile Pro Arg Ile Ala Arg Val
                245                 250                 255

Cys Lys Gly Asp Gln Gly Gly Leu Arg Thr Leu Gln Lys Lys Trp Thr
                260                 265                 270

Ser Phe Leu Lys Ala Arg Leu Ile Cys Ser Arg Pro Asp Ser Gly Leu
            275                 280                 285

Val Phe Asn Val Leu Arg Asp Val Phe Val Leu Arg Ser Pro Gly Leu
        290                 295                 300

Lys Val Pro Val Phe Tyr Ala Leu Phe Thr Pro Gln Leu Asn Asn Val
305                 310                 315                 320

Gly Leu Ser Ala Val Cys Ala Tyr Asn Leu Ser Thr Ala Glu Glu Val
                325                 330                 335

Phe Ser His Gly Lys Tyr Met Gln Ser Thr Val Glu Gln Ser His
                340                 345                 350

Thr Lys Trp Val Arg Tyr Asn Gly Pro Val Pro Lys Pro Arg Pro Gly
            355                 360                 365

Ala Cys Ile Asp Ser Glu Ala Arg Ala Ala Asn Tyr Thr Ser Ser Leu
        370                 375                 380

Asn Leu Pro Asp Lys Thr Leu Gln Phe Val Lys Asp His Pro Leu Met
385                 390                 395                 400

Asp Asp Ser Val Thr Pro Ile Asp Asn Arg Pro Arg Leu Ile Lys Lys
                405                 410                 415

Asp Val Asn Tyr Thr Gln Ile Val Val Asp Arg Thr Gln Ala Leu Asp
                420                 425                 430

Gly Thr Val Tyr Asp Val Met Phe Val Ser Thr Asp Arg Gly Ala Leu
            435                 440                 445

His Lys Ala Ile Ser Leu Glu His Ala Val His Ile Ile Glu Glu Thr
        450                 455                 460

Gln Leu Phe Gln Asp Phe Glu Pro Val Gln Thr Leu Leu Leu Ser Ser
465                 470                 475                 480

Lys Lys Gly Asn Arg Phe Val Tyr Ala Gly Ser Asn Ser Gly Val Val
                485                 490                 495

Gln Ala Pro Leu Ala Phe Cys Gly Lys His Gly Thr Cys Glu Asp Cys
            500                 505                 510

Val Leu Ala Arg Asp Pro Tyr Cys Ala Trp Ser Pro Pro Thr Ala Thr
        515                 520                 525

Cys Val Ala Leu His Gln Thr Glu Ser Pro Ser Arg Gly Leu Ile Gln
        530                 535                 540

Glu Met Ser Gly Asp Ala Ser Val Cys Pro Asp Lys Ser Lys Gly Ser
545                 550                 555                 560

Tyr Arg Gln His Phe Phe Lys His Gly Gly Thr Ala Glu Leu Lys Cys
                565                 570                 575

Ser Gln Lys Ser Asn Leu Ala Arg Val Phe Trp Lys Phe Gln Asn Gly
            580                 585                 590

Val Leu Lys Ala Glu Ser Pro Lys Tyr Gly Leu Met Gly Arg Lys Asn
        595                 600                 605

Leu Leu Ile Phe Asn Leu Ser Glu Gly Asp Ser Gly Val Tyr Gln Cys
        610                 615                 620

Leu Ser Glu Glu Arg Val Lys Asn Lys Thr Val Phe Gln Val Val Ala
625                 630                 635                 640
```

```
Lys His Val Leu Glu Val Lys Val Pro Lys Pro Val Ala Pro
                645                 650                 655

Thr Leu Ser Val Val Gln Thr Glu Gly Ser Arg Ile Ala Thr Lys Val
            660                 665                 670

Leu Val Ala Ser Thr Gln Gly Ser Ser Pro Pro Thr Pro Ala Val Gln
            675                 680                 685

Ala Thr Ser Ser Gly Ala Ile Thr Leu Pro Pro Lys Pro Ala Pro Thr
    690                 695                 700

Gly Thr Ser Cys Glu Pro Lys Ile Val Ile Asn Thr Val Pro Gln Leu
705                 710                 715                 720

His Ser Glu Lys Thr Met Tyr Leu Lys Ser Ser Asp Asn Arg Leu Leu
                725                 730                 735

Met Ser Leu Phe Leu Phe Phe Phe Val Leu Phe Leu Cys Leu Phe Phe
            740                 745                 750

Tyr Asn Cys Tyr Lys Gly Tyr Leu Pro Arg Gln Cys Leu Lys Phe Arg
            755                 760                 765

Ser Ala Leu Leu Ile Gly Lys Lys Pro Lys Ser Asp Phe Cys Asp
    770                 775                 780

Arg Glu Gln Ser Leu Lys Glu Thr Leu Val Glu Pro Gly Ser Phe Ser
785                 790                 795                 800

Gln Gln Asn Gly Glu His Pro Lys Pro Ala Leu Asp Thr Gly Tyr Glu
                805                 810                 815

Thr Glu Gln Asp Thr Ile Thr Ser Lys Val Pro Thr Asp Arg Glu Asp
                820                 825                 830

Ser Gln Arg Ile Asp Asp Leu Ser Ala Arg Asp Lys Pro Phe Asp Val
                835                 840                 845

Lys Cys Glu Leu Lys Phe Ala Asp Ser Asp Ala Asp Gly Asp
850                 855                 860
```

<210> SEQ ID NO 2
<211> LENGTH: 861
<212> TYPE: PRT
<213> ORGANISM: Mus sp.
<220> FEATURE:
<223> OTHER INFORMATION: MOUSE semaphorin-4D

<400> SEQUENCE: 2

```
Met Arg Met Cys Ala Pro Val Arg Gly Leu Phe Leu Ala Leu Val Val
1               5                  10                  15

Val Leu Arg Thr Ala Val Ala Phe Ala Pro Val Pro Arg Leu Thr Trp
            20                  25                  30

Glu His Gly Glu Val Gly Leu Val Gln Phe His Lys Pro Gly Ile Phe
        35                  40                  45

Asn Tyr Ser Ala Leu Leu Met Ser Glu Asp Lys Asp Thr Leu Tyr Val
    50                  55                  60

Gly Ala Arg Glu Ala Val Phe Ala Val Asn Ala Leu Asn Ile Ser Glu
65                  70                  75                  80

Lys Gln His Glu Val Tyr Trp Lys Val Ser Glu Asp Lys Lys Ser Lys
                85                  90                  95

Cys Ala Glu Lys Gly Lys Ser Lys Gln Thr Glu Cys Leu Asn Tyr Ile
            100                 105                 110

Arg Val Leu Gln Pro Leu Ser Ser Thr Ser Leu Tyr Val Cys Gly Thr
        115                 120                 125

Asn Ala Phe Gln Pro Thr Cys Asp His Leu Asn Leu Thr Ser Phe Lys
    130                 135                 140
```

```
Phe Leu Gly Lys Ser Glu Asp Gly Lys Gly Arg Cys Pro Phe Asp Pro
145                 150                 155                 160

Ala His Ser Tyr Thr Ser Val Met Val Gly Glu Leu Tyr Ser Gly
            165                 170                 175

Thr Ser Tyr Asn Phe Leu Gly Ser Glu Pro Ile Ile Ser Arg Asn Ser
            180                 185                 190

Ser His Ser Pro Leu Arg Thr Glu Tyr Ala Ile Pro Trp Leu Asn Glu
        195                 200                 205

Pro Ser Phe Val Phe Ala Asp Val Ile Gln Lys Ser Pro Asp Gly Pro
    210                 215                 220

Glu Gly Glu Asp Asp Lys Val Tyr Phe Phe Thr Glu Val Ser Val
225                 230                 235                 240

Glu Tyr Glu Phe Val Phe Lys Leu Met Ile Pro Arg Val Ala Arg Val
                245                 250                 255

Cys Lys Gly Asp Gln Gly Gly Leu Arg Thr Leu Gln Lys Lys Trp Thr
            260                 265                 270

Ser Phe Leu Lys Ala Arg Leu Ile Cys Ser Lys Pro Asp Ser Gly Leu
        275                 280                 285

Val Phe Asn Ile Leu Gln Asp Val Phe Val Leu Arg Ala Pro Gly Leu
    290                 295                 300

Lys Glu Pro Val Phe Tyr Ala Val Phe Thr Pro Gln Leu Asn Asn Val
305                 310                 315                 320

Gly Leu Ser Ala Val Cys Ala Tyr Thr Leu Ala Thr Val Glu Ala Val
                325                 330                 335

Phe Ser Arg Gly Lys Tyr Met Gln Ser Ala Thr Val Glu Gln Ser His
            340                 345                 350

Thr Lys Trp Val Arg Tyr Asn Gly Pro Val Pro Thr Pro Arg Pro Gly
        355                 360                 365

Ala Cys Ile Asp Ser Glu Ala Arg Ala Ala Asn Tyr Thr Ser Ser Leu
    370                 375                 380

Asn Leu Pro Asp Lys Thr Leu Gln Phe Val Lys Asp His Pro Leu Met
385                 390                 395                 400

Asp Asp Ser Val Thr Pro Ile Asp Asn Arg Pro Lys Leu Ile Lys Lys
                405                 410                 415

Asp Val Asn Tyr Thr Gln Ile Val Val Asp Arg Thr Gln Ala Leu Asp
            420                 425                 430

Gly Thr Phe Tyr Asp Val Met Phe Ile Ser Thr Asp Arg Gly Ala Leu
        435                 440                 445

His Lys Ala Val Ile Leu Thr Lys Glu Val His Val Ile Glu Glu Thr
    450                 455                 460

Gln Leu Phe Arg Asp Ser Glu Pro Val Leu Thr Leu Leu Ser Ser
465                 470                 475                 480

Lys Lys Gly Arg Lys Phe Val Tyr Ala Gly Ser Asn Ser Gly Val Val
                485                 490                 495

Gln Ala Pro Leu Ala Phe Cys Glu Lys His Gly Ser Cys Glu Asp Cys
            500                 505                 510

Val Leu Ala Arg Asp Pro Tyr Cys Ala Trp Ser Pro Ala Ile Lys Ala
        515                 520                 525

Cys Val Thr Leu His Gln Glu Ala Ser Ser Arg Gly Trp Ile Gln
    530                 535                 540

Asp Met Ser Gly Asp Thr Ser Ser Cys Leu Asp Lys Ser Lys Glu Ser
545                 550                 555                 560

Phe Asn Gln His Phe Phe Lys His Gly Gly Thr Ala Glu Leu Lys Cys
```

```
                    565                 570                 575
Phe Gln Lys Ser Asn Leu Ala Arg Val Val Trp Lys Phe Gln Asn Gly
                580                 585                 590

Glu Leu Lys Ala Ala Ser Pro Lys Tyr Gly Phe Val Gly Arg Lys His
            595                 600                 605

Leu Leu Ile Phe Asn Leu Ser Asp Gly Asp Ser Gly Val Tyr Gln Cys
        610                 615                 620

Leu Ser Glu Arg Val Arg Asn Lys Thr Val Ser Gln Leu Leu Ala
625                 630                 635                 640

Lys His Val Leu Glu Val Lys Met Val Pro Arg Thr Pro Ser Pro
                645                 650                 655

Thr Ser Glu Asp Ala Gln Thr Glu Gly Ser Lys Ile Thr Ser Lys Met
                660                 665                 670

Pro Val Ala Ser Thr Gln Gly Ser Ser Pro Thr Pro Ala Leu Trp
            675                 680                 685

Ala Thr Ser Pro Arg Ala Ala Thr Leu Pro Pro Lys Ser Ser Ser Gly
        690                 695                 700

Thr Ser Cys Glu Pro Lys Met Val Ile Asn Thr Val Pro Gln Leu His
705                 710                 715                 720

Ser Glu Lys Thr Val Tyr Leu Lys Ser Ser Asp Asn Arg Leu Leu Met
                725                 730                 735

Ser Leu Leu Leu Phe Ile Phe Val Leu Phe Leu Cys Leu Phe Ser Tyr
                740                 745                 750

Asn Cys Tyr Lys Gly Tyr Leu Pro Gly Gln Cys Leu Lys Phe Arg Ser
            755                 760                 765

Ala Leu Leu Leu Gly Lys Lys Thr Pro Lys Ser Asp Phe Ser Asp Leu
        770                 775                 780

Glu Gln Ser Val Lys Glu Thr Leu Val Glu Pro Gly Ser Phe Ser Gln
785                 790                 795                 800

Gln Asn Gly Asp His Pro Lys Pro Ala Leu Asp Thr Gly Tyr Glu Thr
                805                 810                 815

Glu Gln Asp Thr Ile Thr Ser Lys Val Pro Thr Asp Arg Glu Asp Ser
            820                 825                 830

Gln Arg Ile Asp Glu Leu Ser Ala Arg Asp Lys Pro Phe Asp Val Lys
        835                 840                 845

Cys Glu Leu Lys Phe Ala Asp Ser Asp Ala Asp Gly Asp
        850                 855                 860

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Anti-SEMA4D VHCDR1

<400> SEQUENCE: 3

Gly Tyr Ser Phe Ser Asp Tyr Tyr Met His
1               5                   10

<210> SEQ ID NO 4
<211> LENGTH: 17
<212> TYPE: PRT
<213> ORGANISM: Artificial Sequence
<220> FEATURE:
<223> OTHER INFORMATION: Description of Artificial Sequence: Synthetic
``` peptide
<220> FEATURE:
<223> OTHER INFORMATION: Anti-SEMA4D VHCDR2

<400> SEQUENCE: 4

Gln Ile Asn Pro Thr Thr Gly Gly Ala Ser Tyr Asn Gln Lys Phe Lys
1               5                   10                  15

Gly

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Anti-SEMA4D VHCDR3

<400> SEQUENCE: 5

Tyr Tyr Tyr Gly Arg His Phe Asp Val
1               5

<210> SEQ ID NO 6
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VX/2503 VH

<400> SEQUENCE: 6

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Ser Asp Tyr
                20                  25                  30

Tyr Met His Trp Val Arg Gln Ala Pro Gly Gln Gly Leu Glu Trp Met
            35                  40                  45

Gly Gln Ile Asn Pro Thr Thr Gly Gly Ala Ser Tyr Asn Gln Lys Phe
        50                  55                  60

Lys Gly Lys Ala Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Tyr Tyr Gly Arg His Phe Asp Val Trp Gly Gln Gly Thr
            100                 105                 110

Thr Val Thr Val Ser Ser
        115

<210> SEQ ID NO 7
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mab 67 VH

<400> SEQUENCE: 7

Gln Val Gln Leu Gln Gln Ser Gly Pro Glu Leu Val Lys Pro Gly Ala
1               5                   10                  15

```
Ser Val Lys Ile Ser Cys Lys Ala Ser Gly Tyr Ser Phe Ser Asp Tyr
            20                  25                  30

Tyr Met His Trp Val Lys Gln Ser Pro Glu Asn Ser Leu Glu Trp Ile
        35                  40                  45

Gly Gln Ile Asn Pro Thr Thr Gly Gly Ala Ser Tyr Asn Gln Lys Phe
    50                  55                  60

Lys Gly Lys Ala Thr Leu Thr Val Asp Lys Ser Ser Thr Ala Tyr
65                  70                  75                  80

Met Gln Leu Lys Ser Leu Thr Ser Glu Glu Ser Ala Val Tyr Tyr Cys
                85                  90                  95

Thr Arg Tyr Tyr Tyr Gly Arg His Phe Asp Val Trp Gly Gln Gly Thr
            100                 105                 110

Thr Val Thr Val Ser Ser
        115

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Anti-SEMA4D VL CDR1

<400> SEQUENCE: 8

Lys Ala Ser Gln Ser Val Asp Tyr Asp Gly Asp Ser Tyr Met Asn
1               5                   10                  15

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Anti-SEMA4D VL CDR2

<400> SEQUENCE: 9

Ala Ala Ser Asn Leu Glu Ser
1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Anti-SEMA4D VL CDR3

<400> SEQUENCE: 10

Gln Gln Ser Asn Glu Asp Pro Tyr Thr
1               5

<210> SEQ ID NO 11
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

<223> OTHER INFORMATION: VX/2503 VL

<400> SEQUENCE: 11

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Asp Pro Tyr Thr Phe Gly Gln Gly Thr Lys Leu Glu Ile Lys
            100                 105                 110

<210> SEQ ID NO 12
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mab 67 VL

<400> SEQUENCE: 12

Asp Ile Val Met Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Asp Pro Tyr Thr Phe Gly Gly Gly Thr Lys Leu Glu Ile Lys
            100                 105                 110

<210> SEQ ID NO 13
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mab 76 VH

<400> SEQUENCE: 13

Gln Val Gln Leu Gln Gln Ser Gly Ala Glu Leu Ala Lys Pro Gly Ala
1               5                   10                  15

Ser Val Lys Met Ser Cys Lys Ala Ser Gly Tyr Thr Phe Thr Arg Tyr
            20                  25                  30

Trp Met His Trp Val Lys Gln Arg Pro Gly Gln Gly Leu Glu Trp Ile

```
                    35                  40                  45
Gly Tyr Ile Asn Pro Ser Thr Gly Tyr Ser Asp Tyr Asn Gln Lys Phe
                50                  55                  60

Lys Asp Lys Ala Thr Leu Thr Ala Asp Lys Ser Ser Thr Ala Tyr
 65                  70                  75                  80

Met Gln Leu Ser Ser Leu Thr Ser Glu Asp Ser Ala Val Tyr Tyr Cys
                    85                  90                  95

Ala Arg Asp Pro Tyr Gly Trp Thr Met Asp Ser Trp Gly Gln Gly Thr
                100                 105                 110

Leu Val Thr Val Ser Ser
        115

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Mab76 VHCDR1

<400> SEQUENCE: 14

Gly Tyr Thr Phe Thr Arg Tyr Trp Met His
 1               5                   10

<210> SEQ ID NO 15
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Mab 76 VH CDR2

<400> SEQUENCE: 15

Tyr Ile Asn Pro Ser Thr Gly Tyr Ser Asp Tyr Asn Gln Lys Phe Lys
 1               5                   10                  15

Asp

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Mab 76 VHCDR3

<400> SEQUENCE: 16

Asp Pro Tyr Gly Trp Thr Met Asp Ser
 1               5

<210> SEQ ID NO 17
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mab 76 VL

<400> SEQUENCE: 17
```

-continued

```
Asp Ile Gln Met Thr Gln Ser Pro Ser Ser Leu Ser Ala Ser Leu Gly
1               5                  10                  15

Asp Thr Ile Thr Ile Thr Cys His Ala Ser Gln Asn Ile Asn Val Trp
            20                  25                  30

Leu Ser Trp Tyr Gln Lys Pro Gly Asn Ile Pro Lys Leu Leu Ile
        35                  40                  45

Tyr Lys Ala Ser Asn Leu His Thr Gly Val Pro Ser Arg Phe Ser Gly
50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Gly Gln Ser Tyr Pro Tyr
                85                  90                  95

Thr Phe Gly Gly Gly Thr Lys Leu Glu Ile Lys
            100                 105

<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Mab 76 VL CDR1

<400> SEQUENCE: 18

His Ala Ser Gln Asn Ile Asn Val Trp Leu Ser
1               5                  10

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Mab76 VL CDR2

<400> SEQUENCE: 19

Lys Ala Ser Asn Leu His Thr
1               5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Mab 76 VL CDR3

<400> SEQUENCE: 20

Gln Gln Gly Gln Ser Tyr Pro Tyr Thr
1               5

<210> SEQ ID NO 21
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

<223> OTHER INFORMATION: Human Mab D2517 VH

<400> SEQUENCE: 21

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Phe Ser Asp Tyr
            20                  25                  30

Trp Met Val Trp Val Arg Gln Ala Pro Gly Lys Gly Leu Glu Tyr Val
        35                  40                  45

Ala His Met Asn Gln Asp Gly Gly Ala Arg Tyr Tyr Ala Glu Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Trp Gly Tyr Asp Ser Trp Gly Gln Gly Thr Leu Val
            100                 105                 110

Thr

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Human Mab D2517 HCDR1

<400> SEQUENCE: 22

Asp Tyr Trp Met Val
1               5

<210> SEQ ID NO 23
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Human Mab D2517 HCDR2

<400> SEQUENCE: 23

His Met Asn Gln Asp Gly Gly Ala Arg Tyr Tyr
1               5                   10

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Human Mab D2517 HCDR3

<400> SEQUENCE: 24

Asp Pro Trp Gly Tyr
1               5

<210> SEQ ID NO 25
<211> LENGTH: 104
<212> TYPE: PRT

```
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Mab D2517 VL

<400> SEQUENCE: 25

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Val Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Glu Gln Glu Ala Ala Trp
                85                  90                  95

Val Phe Gly Gly Gly Thr Lys Leu
            100

<210> SEQ ID NO 26
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Human Mab D2517 LCDR1

<400> SEQUENCE: 26

Ser Gly Asp Lys Leu Gly Asp Lys Tyr Ala Val
1               5                   10

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Human Mab D2517 LCDR2

<400> SEQUENCE: 27

Gln Asp Ser Lys Arg Pro Ser
1               5

<210> SEQ ID NO 28
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Human Mab D2517 LCDR3

<400> SEQUENCE: 28

Gln Ala Trp Glu Gln Glu Ala Ala Trp Val
1               5                   10
```